United States Patent
Greenberg

(10) Patent No.: US 7,815,676 B2
(45) Date of Patent: Oct. 19, 2010

(54) APPARATUS AND METHOD FOR ASSISTING IN THE REMOVAL OF A CARDIAC VALVE

(75) Inventor: Roy K. Greenberg, Bratenahl, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 606 days.

(21) Appl. No.: 11/823,050

(22) Filed: Jun. 26, 2007

(65) Prior Publication Data

US 2008/0039881 A1 Feb. 14, 2008

Related U.S. Application Data

(60) Provisional application No. 60/819,021, filed on Jul. 7, 2006.

(51) Int. Cl.
 *A61F 2/24* (2006.01)
(52) U.S. Cl. .................................................. 623/2.11
(58) Field of Classification Search ............. 623/2.11, 623/1.11, 1.12
 See application file for complete search history.

(56) References Cited

U.S. PATENT DOCUMENTS

| | | | | |
|---|---|---|---|---|
| 4,926,858 A | * | 5/1990 | Gifford et al. | 606/159 |
| 5,026,383 A | | 6/1991 | Nobles | |
| 5,047,041 A | | 9/1991 | Samuels | |
| 5,160,342 A | * | 11/1992 | Reger et al. | 606/200 |
| 5,163,953 A | | 11/1992 | Vince | |
| 5,304,189 A | | 4/1994 | Goldberg et al. | |
| 5,370,685 A | | 12/1994 | Stevens | |
| 5,452,733 A | | 9/1995 | Sterman et al. | |
| 5,545,214 A | | 8/1996 | Stevens | |
| 5,571,215 A | | 11/1996 | Sterman et al. | |
| 5,601,580 A | | 2/1997 | Goldberg et al. | |
| 5,662,671 A | * | 9/1997 | Barbut et al. | 606/170 |
| 5,799,661 A | | 9/1998 | Boyd et al. | |
| 5,840,081 A | | 11/1998 | Andersen et al. | |
| 5,846,251 A | * | 12/1998 | Hart | 606/127 |
| 5,855,597 A | | 1/1999 | Jayaraman | |
| 5,885,238 A | | 3/1999 | Stevens et al. | |
| 5,957,949 A | | 9/1999 | Leonhardt et al. | |
| 6,010,531 A | * | 1/2000 | Donlon et al. | 623/2.1 |

(Continued)

FOREIGN PATENT DOCUMENTS

WO WO-2001/035870 A1 5/2001

(Continued)

*Primary Examiner*—Anhtuan T Nguyen
*Assistant Examiner*—Son Dang
(74) *Attorney, Agent, or Firm*—Tarolli, Sundheim, Covell & Tummino LLP

(57) ABSTRACT

An apparatus and method for endovascular removal of a cardiac valve having at least two valve cusps is disclosed. The apparatus is insertable through a blood vessel to access the cardiac valve. The apparatus includes a first catheter assembly for insertion into a blood vessel, deployable cutting means for cutting at least one valve cusp of the cardiac valve, and a deployable filter assembly disposed adjacent the distal end of the first catheter assembly. The first catheter assembly has a longitudinal axis and a distal end. The cutting means is attached to the distal end of the first catheter assembly. The filter assembly is operable to collect the severed valve cusps and is collapsible for removal from the blood vessel with the severed valve cusps retained therein.

63 Claims, 17 Drawing Sheets

U.S. PATENT DOCUMENTS

| | | | |
|---|---|---|---|
| 6,019,739 A | 2/2000 | Rhee et al. | |
| 6,042,554 A | 3/2000 | Rosenman et al. | |
| 6,110,200 A | 8/2000 | Hinnenkamp | |
| 6,149,660 A | 11/2000 | Laufer et al. | |
| 6,168,614 B1 | 1/2001 | Andersen et al. | |
| 6,338,740 B1 | 1/2002 | Carpentier | |
| 6,348,068 B1 | 2/2002 | Campbell et al. | |
| 6,350,282 B1 | 2/2002 | Eberhardt | |
| 6,425,916 B1 | 7/2002 | Garrison et al. | |
| 6,830,584 B1* | 12/2004 | Seguin | 623/2.11 |
| 6,837,901 B2* | 1/2005 | Rabkin et al. | 623/1.11 |
| 6,929,653 B2* | 8/2005 | Strecter | 606/200 |
| 7,371,250 B2* | 5/2008 | Mazzocchi et al. | 606/200 |
| 2002/0082630 A1 | 6/2002 | Menz et al. | |
| 2002/0095116 A1* | 7/2002 | Strecter | 604/96.01 |
| 2002/0151970 A1 | 10/2002 | Garrison et al. | |
| 2003/0216764 A1 | 11/2003 | Tu et al. | |
| 2004/0116951 A1 | 6/2004 | Rosengart | |
| 2004/0225354 A1 | 11/2004 | Allen et al. | |
| 2004/0225355 A1 | 11/2004 | Stevens | |
| 2004/0236418 A1 | 11/2004 | Stevens | |
| 2004/0260322 A1* | 12/2004 | Rudko et al. | 606/167 |
| 2005/0203549 A1 | 9/2005 | Realyvasquez | |
| 2008/0167679 A1* | 7/2008 | Papp | 606/200 |

FOREIGN PATENT DOCUMENTS

WO  WO-2001/049213 A2  7/2001

* cited by examiner

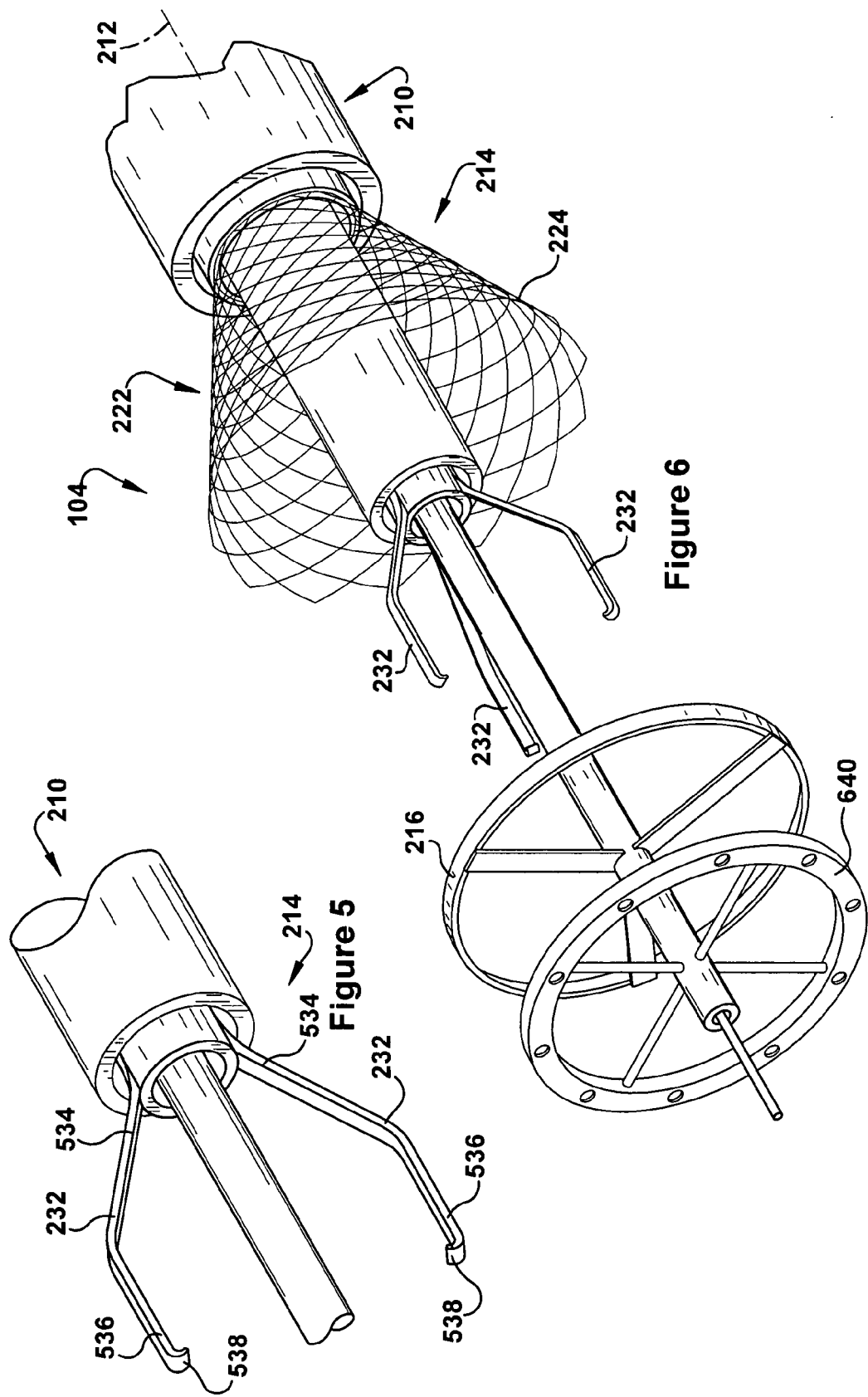

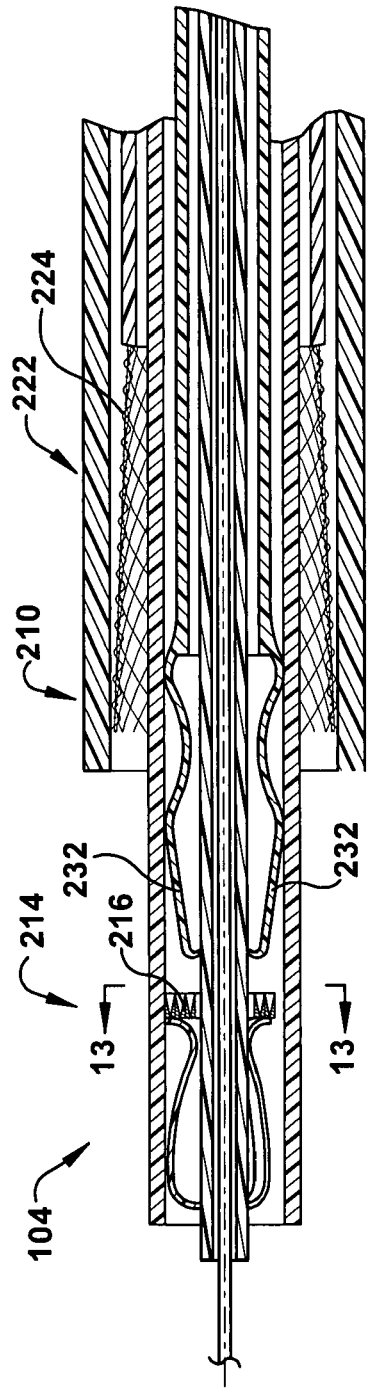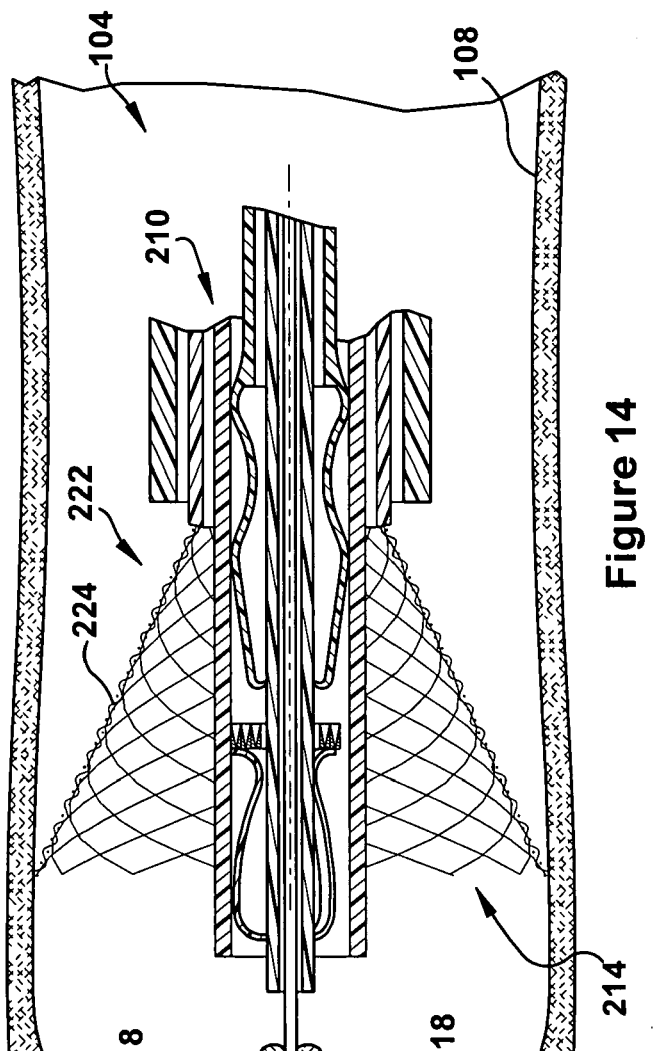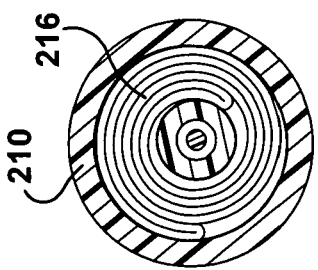

APPARATUS AND METHOD FOR ASSISTING IN THE REMOVAL OF A CARDIAC VALVE

RELATED APPLICATION

This application claims priority from U.S. Provisional Application No. 60/819,021, filed Jul. 7, 2006, the subject matter of which is incorporated hereby reference.

TECHNICAL FIELD

The present invention relates to an apparatus for removing a cardiac valve and a method for use of the apparatus, and, more particularly, to an apparatus and method for assisting in the endovascular removal of a cardiac valve.

BACKGROUND OF THE INVENTION

Replacement cardiac valves are implanted when the patient's native cardiac valve exhibits abnormal anatomy and function due to congenital or acquired valve disease. Congenital abnormalities can be tolerated for years, only to develop into life-threatening problems later. Acquired valve disease may result from various causes such as rheumatic fever, degenerative disorders of the valve tissue, and bacterial or fungal infections.

Valve dysfunction can be classified as either stenosis, in which the valve does not open properly, or insufficiency, in which the valve does not close properly. Stenosis and insufficiency can occur concurrently and both abnormalities increase the workload on the heart in pumping blood through the body. The ability of the heart to function with the increased workload is a major factor in determining whether the valve should be replaced.

When the valve must be replaced using conventional methods, the patient must undergo an invasive, traumatic surgical procedure. The patient's chest is opened with a median sternotomy or major thoracotomy to provide direct access to the heart through a large opening in the chest. The heart is then stopped and the patient is placed on cardiopulmonary bypass using catheters and cannulae inserted directly into the heart and into major blood vessels. The heart, or a blood vessel leading to the heart, is then cut open to access and remove the malfunctioning valve. After removing the valve, the replacement valve is then sewn into place. After the new valve has been implanted, the chest is then closed and the patient is weaned off cardiopulmonary bypass support.

The aforementioned drawbacks to conventional open-chest surgery prevent some patients from undergoing a valve implantation procedure even though a new cardiac valve is needed. Consequently, endovascular valve repair and/or valve replacement procedures that can be performed under local anesthesia in the cardiac catheterization lab, rather than in cardiac surgery, have been developed as they offer tremendous benefits to these patients. Such endovascular procedures for valve replacement often require the removal of the native valve using a minimally invasive, endovascular approach. Hence, a need exists for additional endovascular devices and methods for quickly and accurately removing cardiac valves.

SUMMARY OF THE INVENTION

In a first exemplary embodiment of the present invention, an apparatus for endovascular removal of a cardiac valve having at least two valve cusps is disclosed. The apparatus is insertible through a blood vessel to access the cardiac valve. The apparatus includes a first catheter assembly for insertion into a blood vessel, deployable cutting means for cutting at least one valve cusp of the cardiac valve, and a deployable filter assembly disposed adjacent the distal end of the first catheter assembly and including at least two filter baskets.

The first catheter assembly of the first exemplary embodiment has a longitudinal axis and a distal end. The cutting means is attached to the distal end of the first catheter assembly. The filter assembly is operable to collect the severed valve cusps and is collapsible for removal from the blood vessel with the severed valve cusps retained therein.

In a second exemplary embodiment of the present invention, an apparatus for endovascular removal of a cardiac valve having at least two valve cusps is disclosed. The apparatus is insertible through a blood vessel to access the cardiac valve. The apparatus includes a first catheter assembly for insertion into a blood vessel, cutting means for cutting at least one valve cusp of the cardiac valve, at least two strut members, and a filter assembly disposed adjacent the distal end of the first catheter assembly and including at least one filter basket.

The first catheter assembly of the second exemplary embodiment has a longitudinal axis and a distal end. The cutting means is attached to the distal end of the first catheter assembly and is movable between a radially collapsed first condition and a radially expanded second condition. The strut members each have a first end connected with the first catheter assembly adjacent the distal end and a second end including a cusp hook. The strut members are movable between a collapsed condition and an expanded condition.

The strut members of the second exemplary embodiment, in the expanded condition, are operable to grasp and close the valve cusps of a cardiac valve so that the cutting means can sever the valve cusps through movement of the cutting means in the blood vessel. The filter assembly is movable between a radially collapsed undeployed condition and a radially expanded deployed condition in which the filter assembly is operable to collect the severed valve cusps. The filter assembly is collapsed to the undeployed condition for removal from the blood vessel with the severed valve cusps retained therein.

In a third exemplary embodiment of the present invention, an apparatus for endovascular removal of a cardiac valve having at least two valve cusps is disclosed. The apparatus is insertable through a blood vessel to access the cardiac valve. The apparatus includes a first catheter assembly for insertion into a blood vessel, the first catheter assembly having a longitudinal axis and a distal end, and a second catheter assembly for insertion into a blood vessel, the second catheter assembly having a longitudinal axis and a proximal end. The proximal end of the second catheter assembly is connectable with the distal end of the first catheter assembly adjacent the cardiac valve.

The third exemplary embodiment includes cutting means for cutting at least one valve cusp of the cardiac valve. The cutting means are movable between a radially collapsed first condition and a radially expanded second condition, and are attached to at least one of the distal end of the first catheter assembly and the proximal end of the second catheter assembly.

The third exemplary embodiment also includes at least two strut members. Each of the strut members has a first end connected with at least one of the first catheter assembly, adjacent the distal end, and the second catheter assembly, adjacent the proximal end. Each of the strut members also has a second end comprising a cusp hook, and the strut members are movable between a collapsed condition and an expanded condition. The strut members of the third exemplary embodiment, in the expanded condition, are operable to grasp and close the at least two valve cusps of a cardiac valve so that the cutting means, in the second condition, can sever the valve cusps through movement of the cutting means in the blood vessel.

The third exemplary embodiment also includes a filter assembly disposed adjacent at least one of the distal end of the first catheter assembly and the proximal end of the second catheter assembly and including at least one filter basket. The filter assembly is movable between a radially collapsed undeployed condition and a radially expanded deployed condition in which the filter assembly is operable to collect the severed valve cusps. The filter assembly is collapsed to the undeployed condition for removal from the blood vessel with the severed valve cusps retained therein.

In a fourth exemplary embodiment, a method for endovascular removal of a cardiac valve having at least two valve cusps is disclosed. The method includes the step of providing a first catheter assembly. The first catheter assembly has a cutting means, at least two strut members, and a filter assembly having at least two filter baskets. The cutting means is connected with a distal end of the first catheter assembly, the strut members are connected with the first catheter assembly adjacent the distal end, and the filter assembly is disposed near the distal end of the first catheter assembly.

The method of the fourth exemplary embodiment includes the steps of inserting the distal end of the first catheter assembly through a blood vessel with the cutting means, the strut members, and the filter assembly in respective radially collapsed conditions; advancing the distal end of the first catheter assembly through the cusps of a cardiac valve so that the cutting means, the strut members, and the filter assembly are located adjacent the cusps; and expanding the cutting means, the strut members, and the filter assembly to respective radially expanded conditions.

The method of the fourth exemplary embodiment also includes the steps of hooking the cusps of the cardiac valve with the cusp hooks on the strut members; engaging the roots of the cusps of the cardiac valve with the cutting means; and severing the cusps at or near their roots through movement of the cutting means. The method also includes the steps of pulling the strut members into the filter assembly and collecting the severed cusps in the filter assembly; collapsing the cutting means, the strut members, and the filter assembly to their respective radially collapsed conditions; and withdrawing the distal end of the first catheter assembly from the blood vessel with the severed valve cusps retained within the filter assembly.

In a fifth exemplary embodiment of the present invention, a method for endovascular removal of a cardiac valve having at least two valve cusps is disclosed. The method includes the step of providing a first catheter assembly having a distal end with cutting means connected at the distal end. The cutting means is movable between a radially collapsed first condition and a radially expanded second condition. The first catheter assembly further includes at least two strut members and a filter assembly, the strut members being attached to the first catheter assembly adjacent the distal end. Each of the strut members has an end including a cusp hook. The strut members are each movable between a collapsed condition and an expanded condition. The filter assembly has at least two filter baskets and is disposed near the distal end of the first catheter assembly. The filter assembly is movable between a radially collapsed undeployed condition and a radially expanded deployed condition.

The method of the fifth exemplary embodiment includes the steps of placing the cutting means in the first condition; placing the strut members in the collapsed condition; placing the filter assembly in the undeployed condition; and inserting the distal end of the first catheter assembly through a blood vessel.

The method of the fifth exemplary embodiment also includes the steps of advancing the distal end of the first catheter assembly through the cusps of a cardiac valve so that the cutting means, the strut members, and the filter assembly are located adjacent the cusps; deploying the filter assembly to the deployed condition; expanding the filter baskets of the filter assembly, adjacent each other along the first catheter assembly, to respective frustoconical shapes; and expanding the cutting means to the second condition.

The method of the fifth exemplary embodiment also includes the steps of moving the strut members to the expanded condition and into engagement with the cusps of the cardiac valve; hooking the cusps of the cardiac val roots through movement of the cutting means.

The method of the fifth exemplary embodiment also includes the steps of pulling the strut members into the filter assembly and collecting the severed cusps, which are attached to the strut members, in the filter assembly; collapsing the at least two strut members to the collapsed condition; collapsing the filter assembly to the undeployed condition with the valve cusps contained therein; collapsing the cutting means to the first condition; and withdrawing the distal end of the first catheter assembly from the blood vessel with the severed valve cusps retained within the filter assembly in the undeployed condition.

BRIEF DESCRIPTION OF THE DRAWINGS

For a better understanding of the invention, reference may be made to the accompanying drawings, in which:

FIG. 5 is a perspective view of one part of the apparatus of FIG. 2;

FIG. 6 is a perspective view of one part of the apparatus of FIG. 2;

FIG. 12 is a side view, taken in section, of the apparatus of FIG. 2 in a fully collapsed condition;

FIG. 13 is a sectional view taken along line 13-13 in FIG. 12;

FIG. 14 is a side view similar to FIG. 12 illustrating the apparatus in a partially deployed condition in a blood vessel adjacent a cardiac valve;

DESCRIPTION OF EMBODIMENTS

Figure 1:
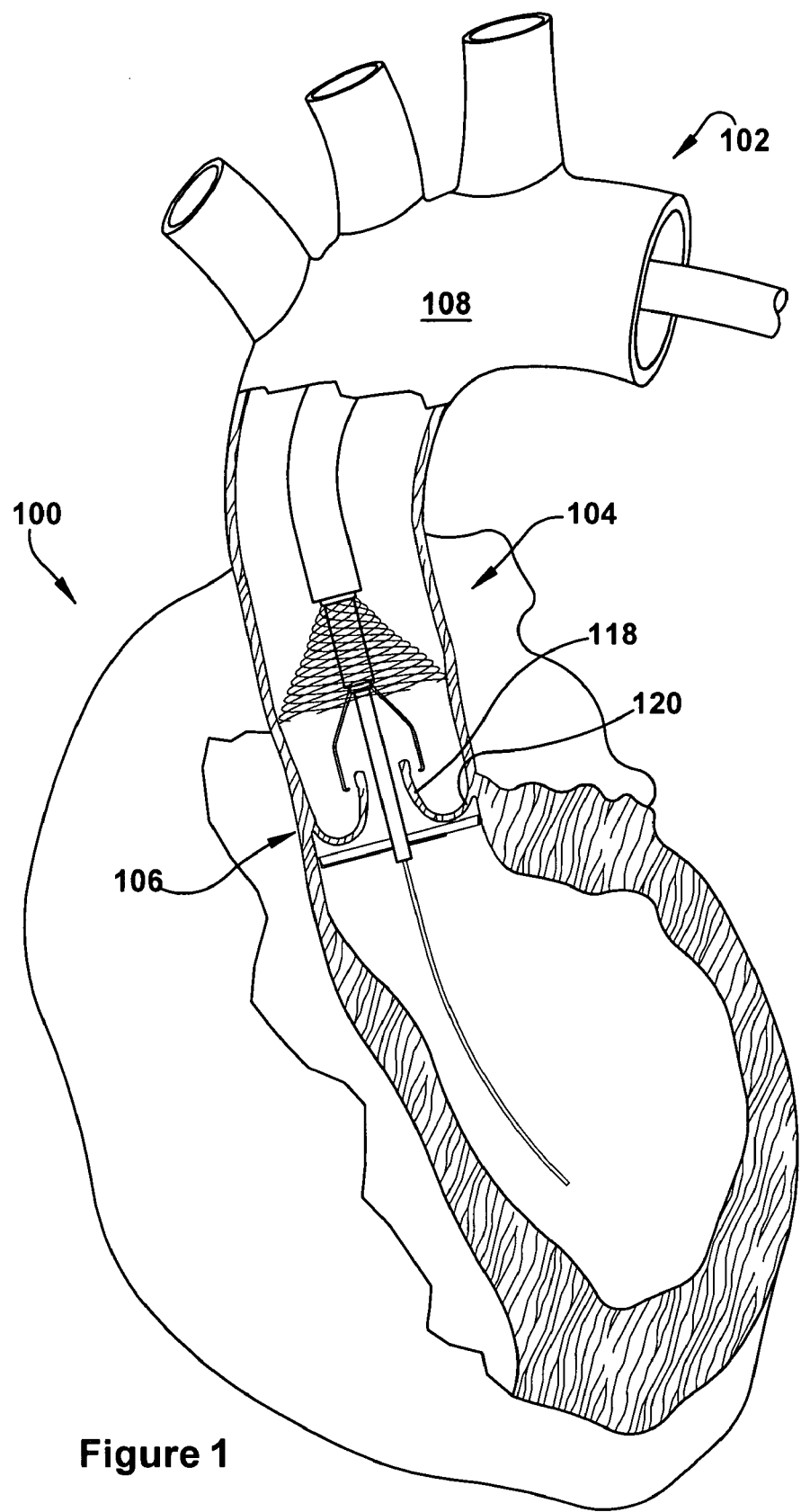
FIG. 1 is a schematic side view, partly in section, of a heart and associated aortic arch with an apparatus for assisting in the removal of a cardiac valve in accordance with an exemplary embodiment of the present invention.

In accordance with the present invention, FIG. 1 depicts a partial view of a heart 100 and aortic arch 102 including an exemplary embodiment of an apparatus 104 for endovascular removal of a cardiac valve 106 from the heart 100. The apparatus 104 is insertible through a blood vessel 108, shown in FIG. 1 as an aorta 108 of the heart 100 but optionally any suitable blood vessel 108, to access the cardiac valve 106. The apparatus 104 is shown in more detail in FIG. 2 in a deployed condition.

The apparatus 104 includes a first catheter assembly 210 for insertion into the blood vessel 108. The first catheter assembly 210 has a longitudinal axis 212, a distal end 214, and a proximal end (not shown) spaced apart from the distal end 214. The distal end 214 enters the body by insertion into the blood vessel 108 at a location spaced apart from the heart 100, via a known procedure generally used for endovascular surgery. The first catheter assembly 210 may include a single catheter tube, a series of concentric catheter tubes of differing sizes, several small catheter tubes located adjacent one another and substantially within an outer catheter tube, or any other suitable configuration to contain, deliver, and operate the elements of the apparatus 104 in a desired manner. Likewise, the various catheter tubes making up the first catheter assembly 210 may each have independent relative longitudinal motion as needed for desired function of the apparatus 104. For example, the catheter tubes of the first catheter assembly 210 could be inserted to or removed from the blood vessel 108 either sequentially/in series or simultaneously/in parallel. The mechanisms of catheter insertion and operation are known to one of ordinary skill in the art and will not be further discussed.

A deployable cutting means 216 is attached to the distal end 214 of the first catheter assembly. The cutting means 216 may be movable between a radially collapsed first condition and a radially expanded second condition. Optionally, the cutting means 216 substantially spans a diameter of the blood vessel 108 when in the second condition.

FIGS. 3A-3F depict various examples of suitable cutting means 216. In addition to the exemplary embodiments shown in FIGS. 3A-3F, the cutting means 216 may comprise a multi-piece configuration such as a blade and anvil or two blades which cut material placed therebetween, a noncontact means such as a cutting laser, a highly flexible means such as a rapidly spinning sharpened wire, an abrading means such as a sanding disk, or any other suitable cutting means 216.

Each cardiac valve 106 includes two or more valve cusps 118, shown in FIG. 1. Each valve cusp 120 has a root 120 which is connected with the blood vessel 108. The valve cusps 118 open and close in a known manner to control movement of blood through the blood vessel 108. When the cardiac valve 106 is "removed", the actual procedure involves severing at least a portion of each valve cusp 118 from the blood vessel 108. This severance may occur at the root 120 of the valve cusp 118 and be substantially complete or may instead be a partial severance, in which a portion of the valve cusp 118 is intentionally left attached to the blood vessel 108. Both situations are intended to be referenced in this description and claims by general use of the term "sever"; modification by "partial" will be clearly indicated here when applicable.

In most cases, a surgeon will desire to leave the wall of the blood vessel 108 intact at the cardiac valve 106 location, possibly to facilitate later installation of a prosthetic valve (not shown) and to avoid unwanted leakage of blood from the blood vessel 108. Therefore, it is desirable for the cutting means 216 to primarily present a blunt or otherwise non-cutting edge to the blood vessel 108 and to be adapted for precise control by the surgeon.

Regardless of the cutting means 216 used, once the valve cusps 118 are severed, they must be captured and removed from the blood vessel 108. Otherwise, natural flow of blood will carry the severed valve cusps 118 away from the heart 100 and to another part of the body, where they may create an unwanted blockage. In addition, severance of the valve cusps 118 may create valve removal debris (not shown), which is made up of small particles of valve cusp 118, plaque buildup, calcifications or a thrombus from the valve cusp 118 or blood vessel 108, and other loose matter. The valve removal debris can swirl in the blood around the cardiac valve site, possibly becoming temporarily trapped in small cavities or openings in the heart structure, and eventually be carried by the natural bloodflow away from the heart 100 and to another part of the body in an unwanted manner. Therefore, a deployable filter assembly 222 may be provided to substantially capture the severed valve cusps 118 and valve removal debris upon removal of the cardiac valve.

The filter assembly 222 is disposed adjacent the cutting means 216 and includes at least one filter basket 224 (only one shown in most Figures, for clarity). The filter assembly 222 may be selectively moved between a radially collapsed first condition and a radially expanded second condition. In the second condition, the filter assembly 222 optionally spans a substantial portion of the cross-section of the blood vessel 108. The filter assembly 222 in the second condition collects at least one severed valve cusp 118 and then is collapsible to the first condition for removal from the blood vessel 108 with the severed valve cusps 118 retained therein. The filter assembly 222 may include a repository bag (not shown), into which at least one severed valve cusp 118 may be maneuvered for removal from the body. The repository bag, when present, is optionally porous enough to provide filtration in addition to the filter basket(s) 224.

Figure 2:
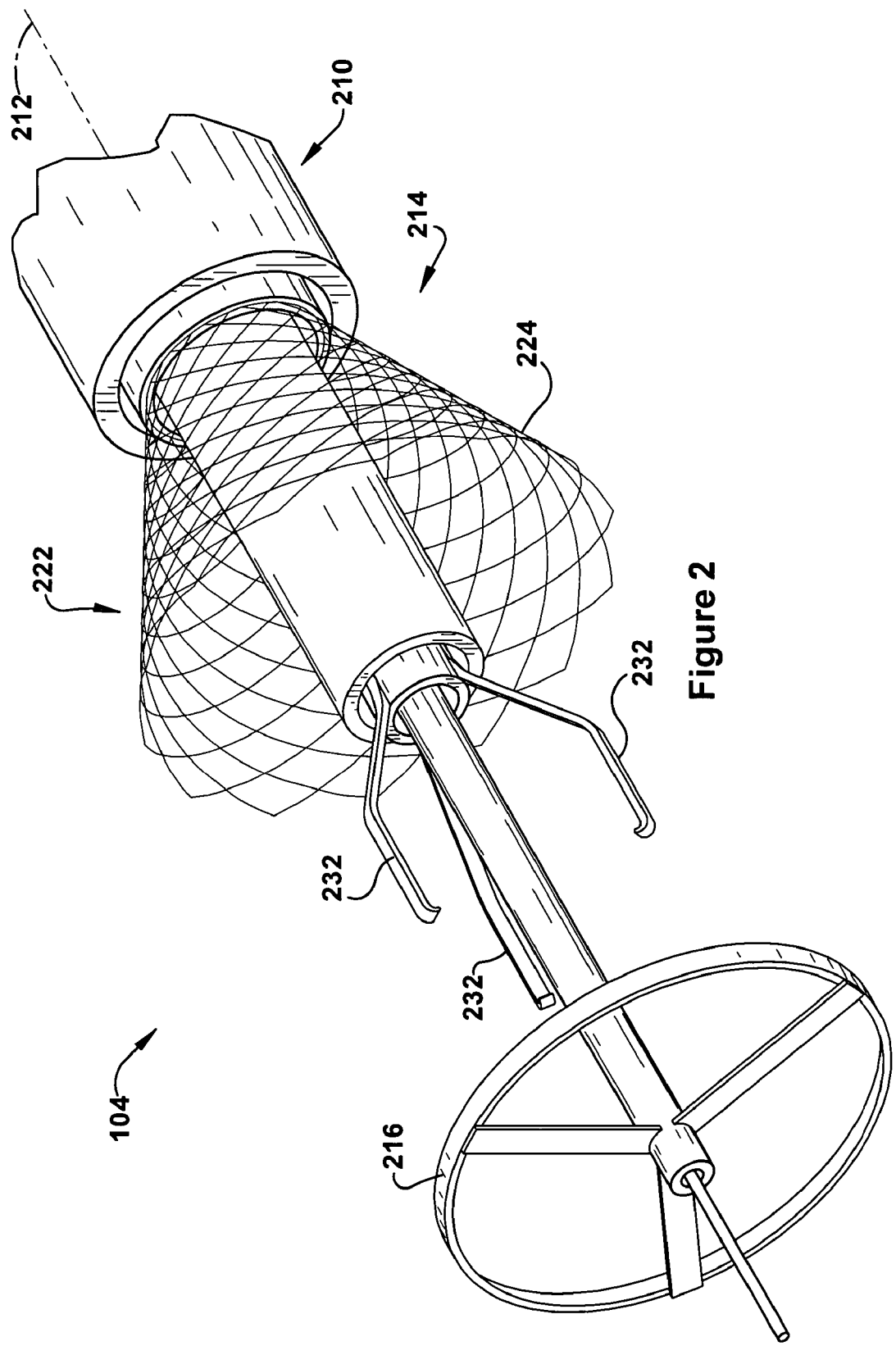
FIG. 2 is a perspective view illustrating the apparatus of FIG. 1 in a fully deployed condition.
Figure 3A:
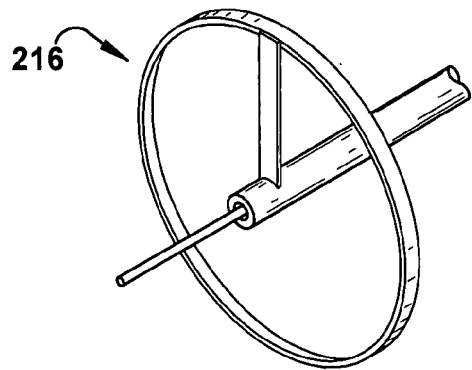
FIGS. 3A-3F are perspective views of alternate constructions for one part of the apparatus of FIG. 2.
Figure 3B:
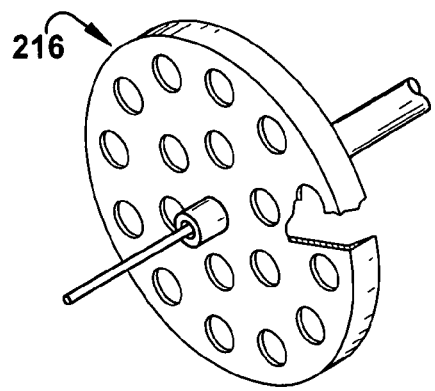
Figure 3C:
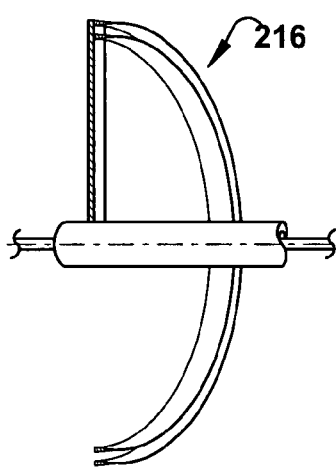
Figure 3D:
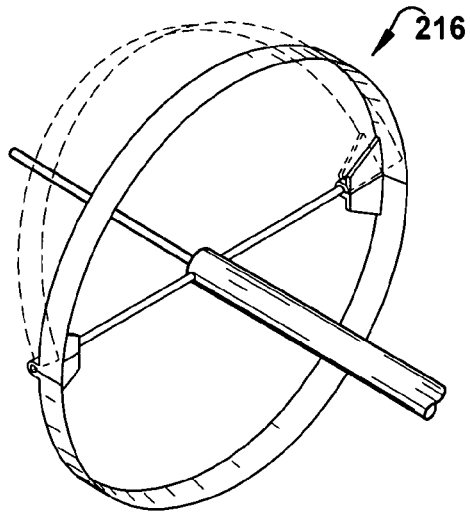
Figure 3E:
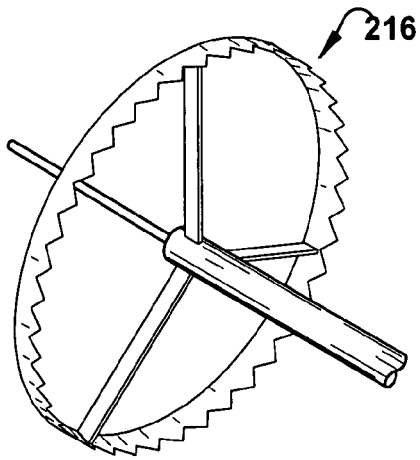
Figure 3F:
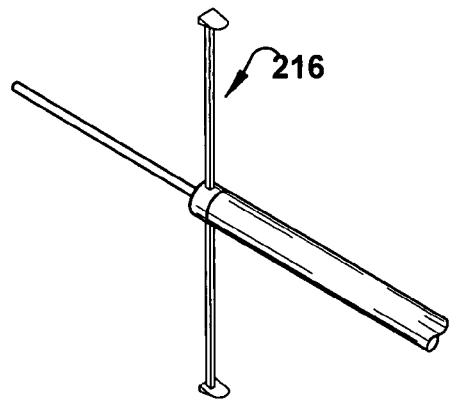
Figure 4A:
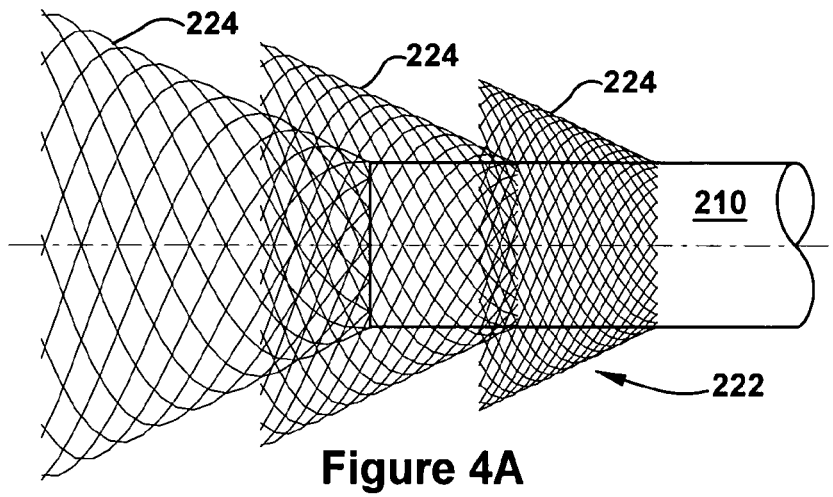
FIGS. 4A-4C are side views of alternate constructions for one part of the apparatus of FIG. 2.

Each filter basket 224 may have a frustoconical shape, as shown in FIG. 2. Also, when two or more filter baskets 224 are present, they may have differing porosities to filter blood flowing through the blood vessel 108 in a desired manner, as shown in FIG. 4A.

Optionally, two or more filter baskets 224 are disposed adjacent each other along the longitudinal axis 212 of the first catheter assembly 210. These adjacent filter baskets 224 may axially overlap at least a portion of each other when deployed. By "axially overlap", what is meant is that, in a view taken along a line parallel to the longitudinal axis 212, at least a portion of each the two or more filter baskets 224 appears to be superimposed on the other filter basket(s) 224. However, the filter baskets 224 are not required to be coaxial, symmetrical, identical, or otherwise matched. For example, the filter baskets 224 may have different dimensions/shapes/porosities from each other as needed to effectively capture the severed valve cusps 118 and/or valve removal debris in the portion of the blood vessel 108 where each filter basket 224 is located. In addition, the filter baskets 224 need not appear to overlap or nest/stack together when viewed in a direction perpendicular to the longitudinal axis 212. Finally, the filter baskets 224 may be deployed into any desired orientation or position with respect to the cardiac valve 106.

Figure 4B:
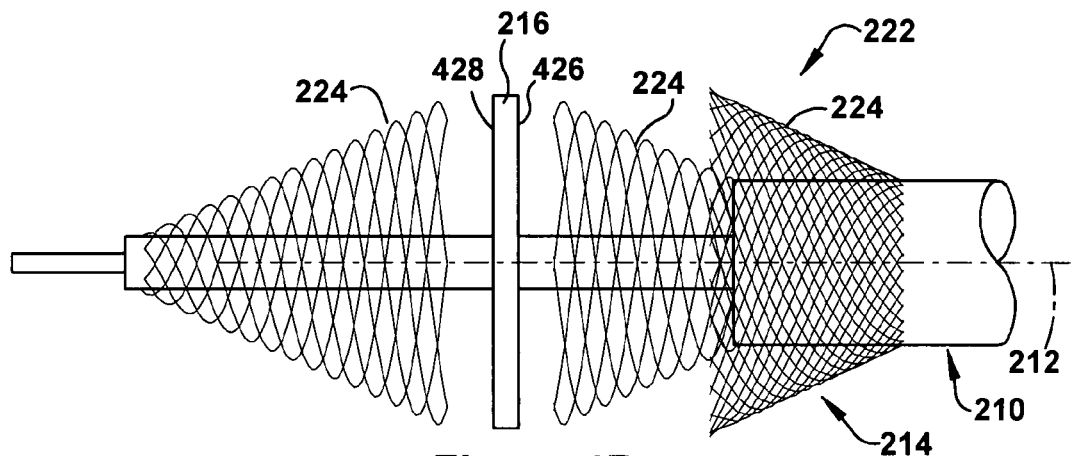

When first and, optionally, second filter baskets 224 are located adjacent a first side 426 of the cutting means 216, a third filter basket 224 may be located adjacent a second side 428 of the cutting means 216 which is longitudinally spaced from the first side 426, as shown in FIG. 4B. The cardiac valve 106 may be located longitudinally between the third filter basket 224 and the first and second filter baskets 224 within the blood vessel 108. If the third filter basket 224 has a frustoconical shape, as in the exemplary embodiment shown in FIG. 4B, the open end of the third filter basket 224 may either face in the opposite direction as the first and second filter baskets 224, as in the FIG. 4B arrangement, or may face in the same direction as the first and second filter baskets 224 (not shown), as desired for a particular application of the claimed apparatus 104.

Figure 4C:
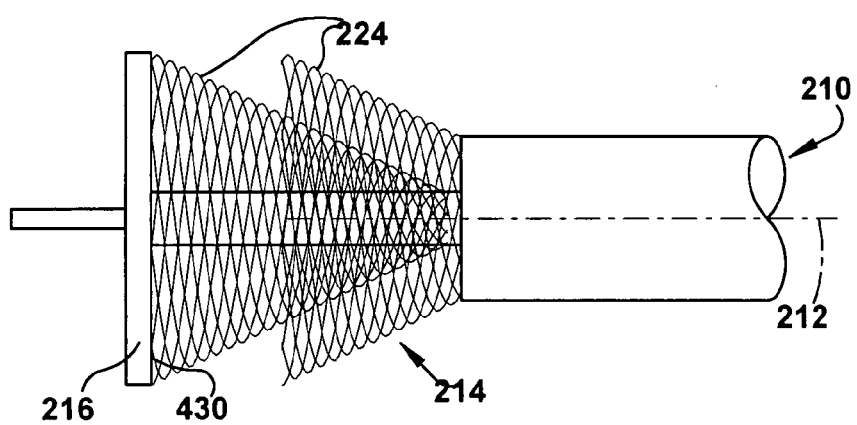

Optionally, and as shown in the exemplary embodiment of FIG. 4C, at least one filter basket 224 includes a filter rim 430 spaced radially apart from the distal end 214 of the first catheter assembly 210, and the filter rim 430 includes the cutting means 216. The filter basket 224 including the cutting means 216 is located adjacent the cardiac valve 106. When this combination filter basket/cutting means 224/216 arrangement is present, there may also be at least one additional filter basket 224 longitudinally spaced from the first filter basket 224, as shown in FIG. 4C, for ease in collecting the severed valve cusps 118 and valve removal debris.

The apparatus 104 of FIG. 2 may include two or more strut members 232, shown in greater detail in FIG. 5. Each of the strut members 232 has a first end 534 connected with the first catheter assembly 210 adjacent the distal end 214. Each strut member 232 also has a second end 536 including a cusp hook 538. The strut members 232 are operable to grasp and close the valve cusps 118 of the cardiac valve 106 therebetween so that the cutting means 216 can sever the valve cusps 118.

Each strut member 232 optionally is associated with a different valve cusp 118 of the native cardiac valve, though each valve cusp 118 may be associated with more than one strut member 232. Therefore, for a two-cusp valve, at least a pair of strut members 232 could be spaced apart about the longitudinal axis 212 of the first catheter assembly 210, as shown in FIG. 5. Likewise, for a three-cusp valve, at least three strut members 232 could be spaced apart about the longitudinal axis 212, as shown in FIG. 2. A sheath (not shown) may encircle the strut members 232 within the first catheter assembly 210 to contain the strut members 232 for insertion and retraction through the first catheter assembly 210.

Each cusp hook 538 may simply be a bent terminus of the second end 536 of the strut member 232, as in the exemplary embodiment of the Figs., or may include a textured/serrated gripping surface, a multi-piece movable grabber or pincher, an adhesive pad, a suction tip, or any other suitable means for grasping a valve cusp 118 in the desired manner. In addition, the cusp hook 538 may be selected to either pierce or avoid piercing the valve cusp 118, as required by a particular application of the apparatus 104. The precise nature of the cusp hook 538 is not essential to the present invention.

The apparatus 104 also may include means (not shown) for moving the strut members 232 between a radially collapsed first condition and a radially expanded second condition. For instance, the strut members 232 may be moved between the first and second conditions by a spring-loaded device. The strut members 232 may also or instead be made of spring steel or a memory-alloy material which naturally moves between the first and second conditions responsive to a length of the strut member 232 protruding from the distal end 214 of the first catheter assembly 210, possibly with the assistance of a spreader member (not shown). The strut members 232 optionally are collapsible to the first condition with the severed valve cusps 118 attached to the cusp hooks 538 for retraction and removal through the blood vessel 108.

As shown in FIG. 6, a suction device 640 may be disposed adjacent the cutting means 216. The suction device 640 is adapted to draw at least one of the valve removal debris and one or more severed valve cusps 118 into the first catheter assembly 210. Optionally, the suction device may be located to draw at least one of the valve removal debris and one or more severed valve cusps 118 into the filter assembly 222. The suction device 640 may be used when the blood flow through the heart 100 is stopped during the valve removal process and natural blood flow cannot assist in removing the valve removal debris and severed valve cusps 118 from the heart 100.

The suction device 640 may be a suction ring 640, as depicted in the example embodiment of FIG. 6, which is selectively spaced radially apart from the distal end of the first catheter assembly. Alternatively, the suction device 640 may be an aspiration tube (not shown) located within the first catheter assembly 210 and adapted for longitudinal motion to a desired suction position adjacent the cutting means 216. Optionally, the suction ring 640 is connected with a filter rim 430 of a filter basket 224 (not shown), such that the valve removal debris and/or severed valve cusps 118 are drawn by suction into the filter basket 224 for removal through the blood vessel 108.

Figure 7A:
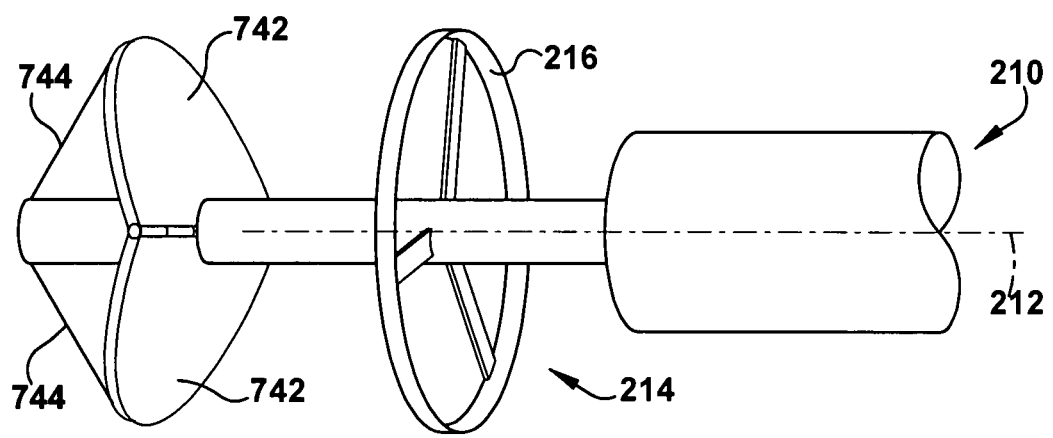
FIGS. 7A-7B are side views of alternate constructions for one part of the apparatus of FIG. 2.
Figure 7B:
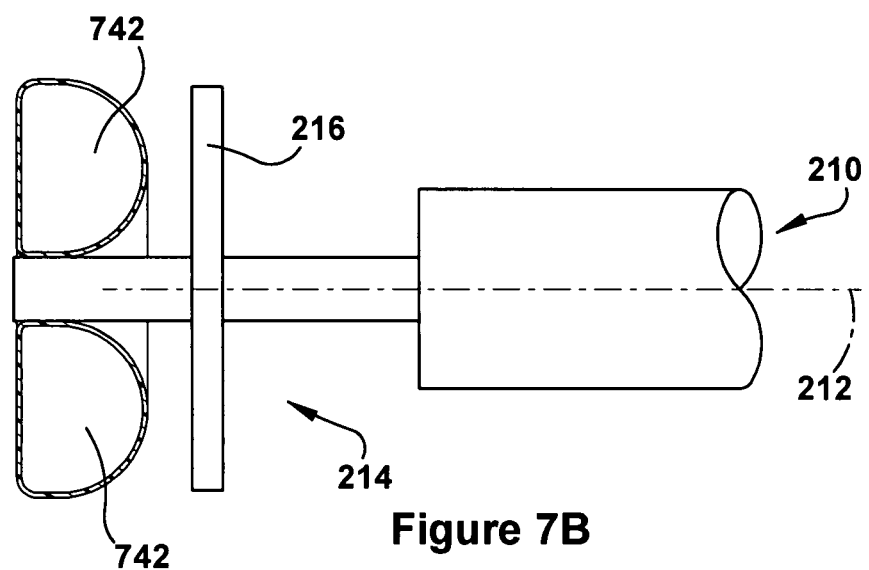

As shown in FIG. 7A, at least one flap 742 may be located at the distal end 214 of the first catheter assembly 210. The flap 742 is operable to function as a temporary valve cusp 118 after the cardiac valve 106 has been severed. The flap 742 need not operate in the same manner as does the native valve cusp 118 of the cardiac valve 106, but may operate instead in any suitable manner. For example and as in the FIG. 7A embodiment, each flap 742 could have an associated flap cord 744 (shown in dotted line in FIG. 7A) which changes in length responsive to some external stimulus to assist the flap 742 in motion simulating the function of the native valve cusp 118. Another exemplary embodiment is shown in FIG. 7B, in which the flap 742 is a balloon 742, which may be selectively inflated and deflated to function as a temporary valve cusp 118.

Optionally, and as shown in the example embodiments of FIGS. 8-11, a second catheter assembly 846 is adapted for insertion into a blood vessel 108, which may be a different blood vessel 108 than the blood vessel 108 into which the first catheter assembly 210 is inserted. Features of FIGS. 8-11 that are the same as, or similar to, those described with regard to FIGS. 1-7 are given the same reference numbers with the addition of a prime.

The second catheter assembly 846 has a longitudinal axis 212', a proximal end 848, and a distal end (not shown) spaced apart from the proximal end 848 along the longitudinal axis 212'. The proximal end 848 enters the body by insertion into the blood vessel 108' at a location spaced apart from the heart 100, via a known procedure generally used for endovascular surgery. The second catheter assembly 846 may include a single catheter tube, a series of concentric catheter tubes of differing sizes, several small catheter tubes located adjacent one another within an outer catheter tube, or any other suitable configuration to contain, deliver, and operate the elements of the apparatus 104 in a desired manner. Likewise, the various catheter tubes making up the second catheter assembly 846 may each have independent relative longitudinal motion as needed for desired function of the apparatus 104. The mechanisms of catheter insertion and operation are known to one of ordinary skill in the art and will not be further discussed.

Figure 8:
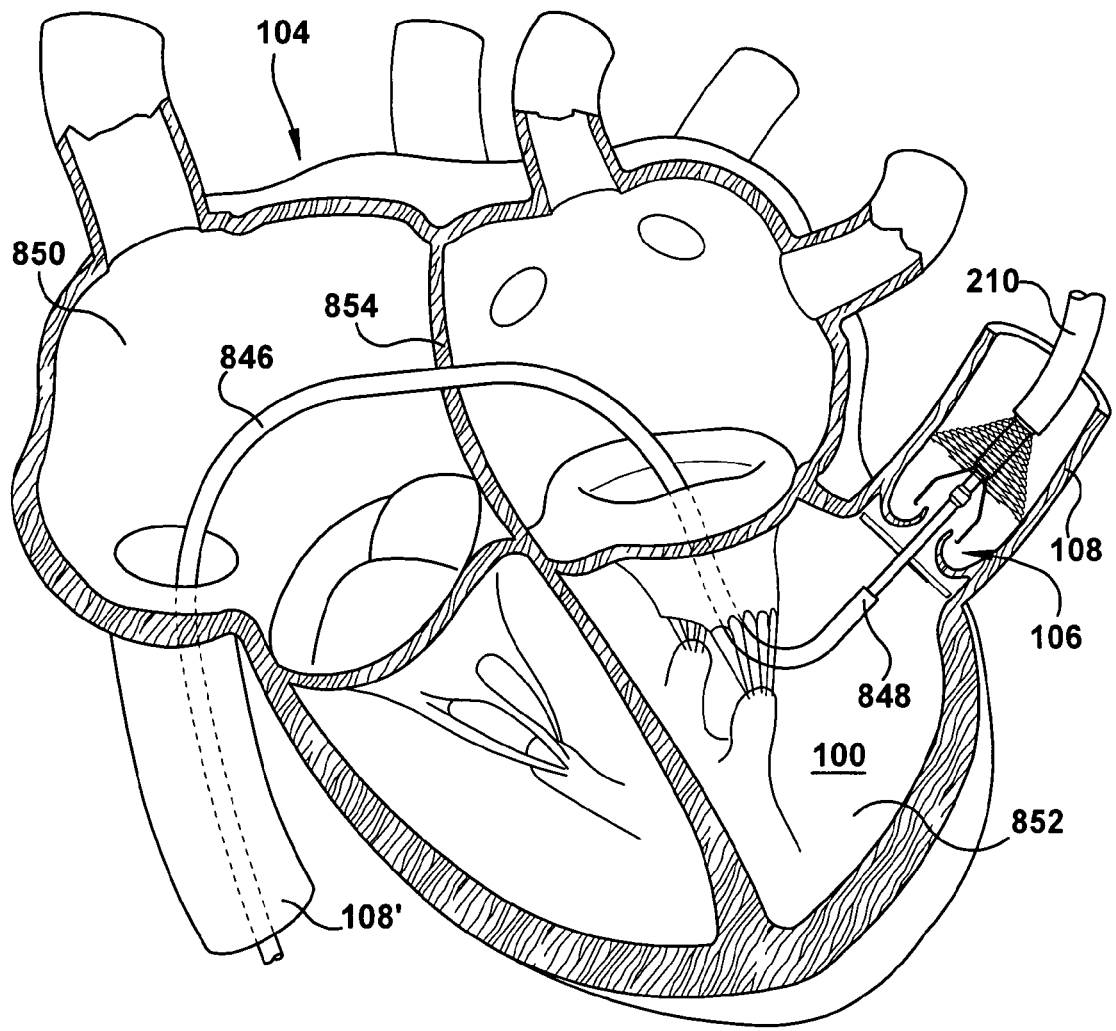
FIG. 8 is a schematic side view, partly in section, of a heart with an apparatus for assisting in the removal of a cardiac valve in accordance with another exemplary embodiment of the present invention.

The second catheter assembly 846 may enter the heart 100 via a different heart chamber 850 than the heart chamber 852 in which the first catheter assembly 210 is positioned. In such case, as depicted in FIG. 8, the second catheter assembly 846 may pass through any suitable internal heart wall 854 in a known manner to position the proximal end 848 of the second catheter assembly 846 as desired.

Figure 9:
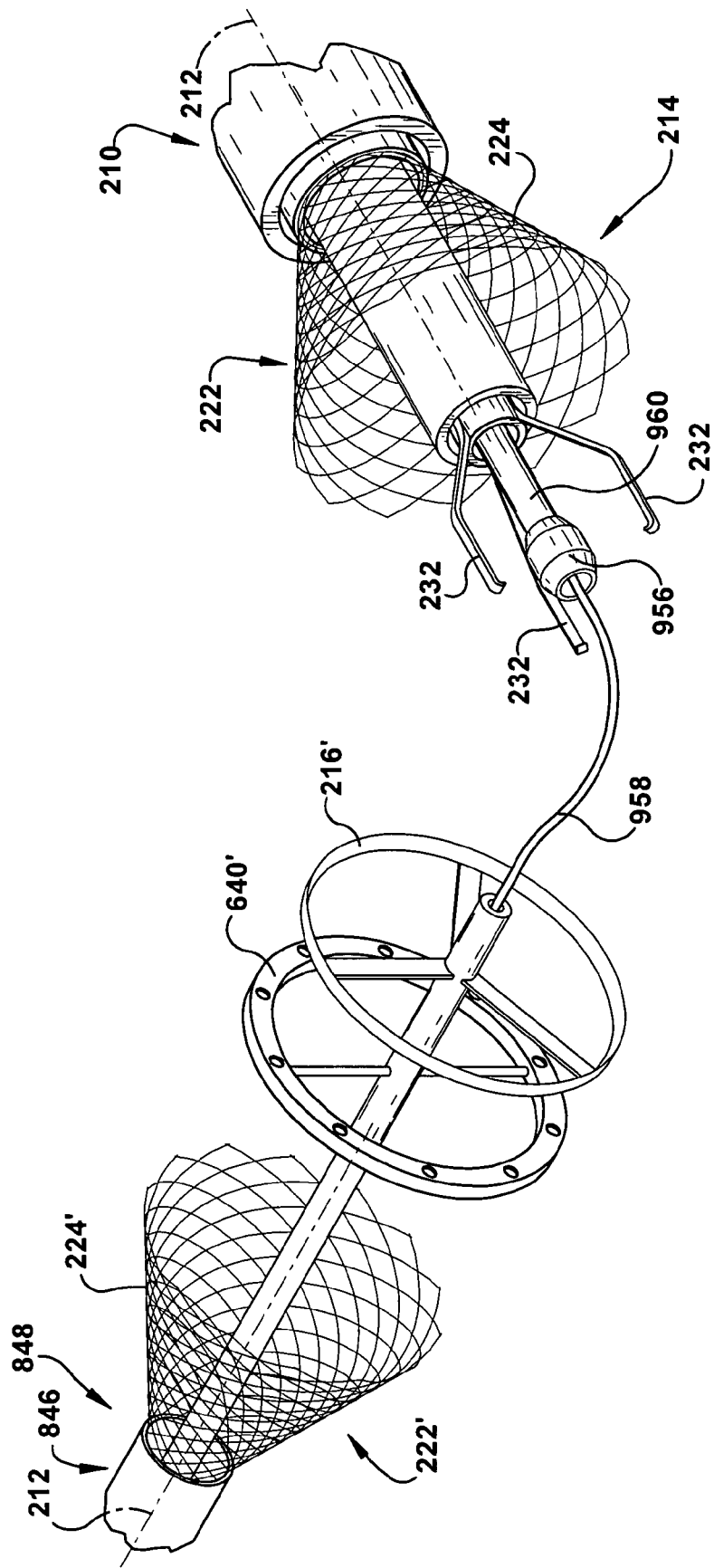
FIG. 9 is a perspective view illustrating the apparatus of FIG. 8 in a fully deployed condition.

The proximal end 848 of the second catheter assembly 846 may be connected with the distal end 214 of the first catheter assembly 210 adjacent the cardiac valve 106 to form the apparatus 104, an exemplary embodiment of which is shown in greater detail in FIG. 9. The interface between the first and second catheter assemblies 210 and 846 may be located within a blood vessel 108, 108' or within a heart chamber 852, 854 during connection. Such connection may be accomplished with the aid of a coupler 956 linking a guide member 958 extending from the proximal end 848 of the second catheter assembly 846 with a coupling member 960 extending from the distal end 214 of the first catheter assembly 210. In the exemplary embodiment of FIG. 9, the coupler 956 is associated with the coupling member 960 of the first catheter assembly 210, but the coupler 956 could be associated with any suitable structure of either or both of the first or second catheter assemblies 210 or 846.

For example, the guide member 958 could include a hook end adapted to mate with a hole in the coupler 956 and thereby connect the first and second catheter assemblies 210 and 846. The connection can be accomplished through any suitable coupler 956 structure, including but not limited to magnetic, interference/frictional fit, captured-ball or other mechanical arrangement, or adhesive means. The first and second catheter assemblies 210 and 846 need not be connected together to still collectively form the apparatus 104, but when such a connection is made, it is anticipated that at least a portion of the two-piece connected apparatus 104 will extend longitudinally through the native cardiac valve 106.

When present, the second catheter assembly 846 may have associated therewith any or all of the deployable structures of the apparatus 104 discussed previously in relation to the first catheter assembly 210, and in any suitable order along the longitudinal axes 212 and 212'. For example, a filter basket 224' (which may also function as a temporary valve), suction ring 640', and cutting means 216' are provided adjacent the proximal end 848 of the second catheter assembly 846 in the exemplary embodiment of FIG. 9.

Structures having longitudinal direction-specific features, such as the filter basket 224' and cutting means 216', may be oriented either toward or away from the first catheter assembly 210 along the longitudinal axes 212 and 212' without harm to the present invention. For example, one filter basket 224', as shown in FIG. 9, is disposed adjacent the proximal end 848 of the second catheter assembly 846 and may have its open end pointing toward the first catheter assembly 210 as shown in FIG. 9 or may be reversed so that the open end is oriented instead away from the first catheter assembly 210.

Figure 10:
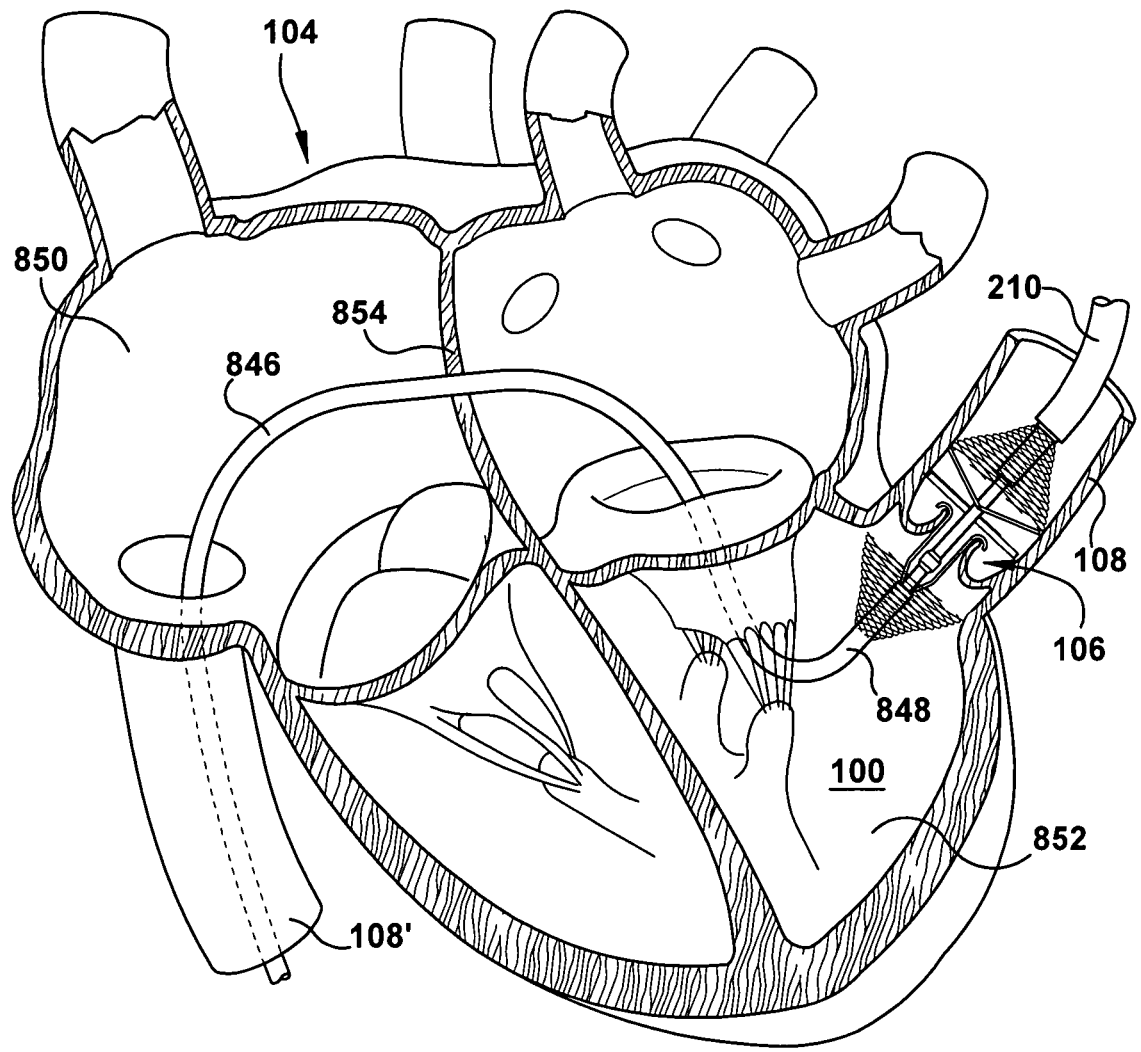
FIG. 10 is a schematic side view, partly in section, of a heart with an apparatus for assisting in the removal of a cardiac valve in accordance with another exemplary embodiment of the present invention.
Figure 11:
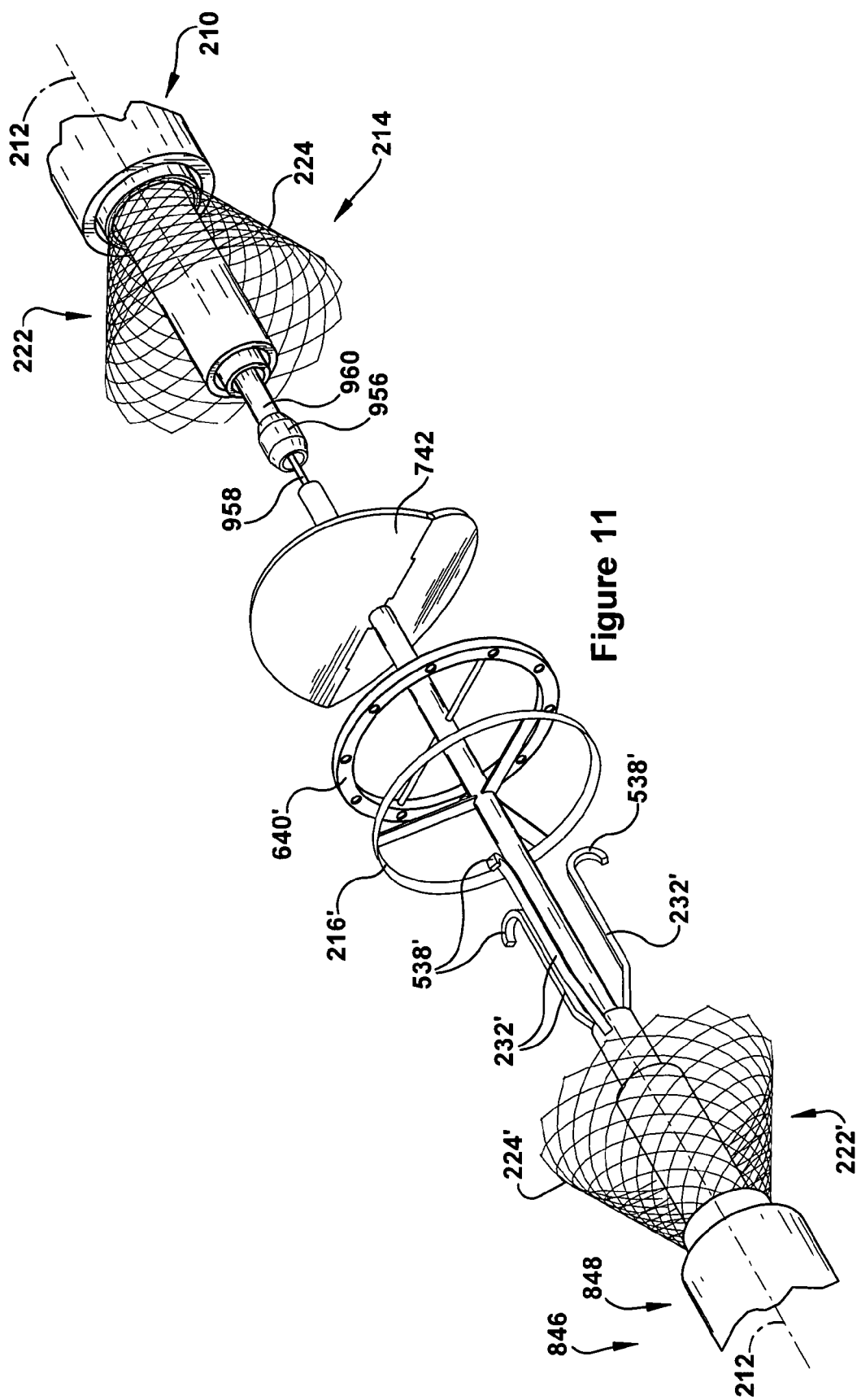
FIG. 11 is a perspective view illustrating the apparatus of FIG. 10 in a fully deployed condition.

The apparatus 104 shown in FIGS. 10-11 is similar to that shown in FIGS. 8-9. However, the second catheter assembly 846 depicted in FIGS. 10-11 includes different deployable structures of the apparatus 104 than those associated with the second catheter assembly 846 of FIGS. 8-9 and illustrates an optional alternate configuration of the apparatus 104 of the present invention. For example, a filter basket 224', a suction ring 640', temporary valve flaps 742, and cutting means 216' are provided adjacent the proximal end 848 of the second catheter assembly 846 in the exemplary embodiment of FIGS. 10-11.

In addition, and as best depicted in FIG. 11, the second catheter assembly 846 may include strut members 232'. The strut members 232' are operable to grasp and close the valve cusps 118 of the cardiac valve 106 therebetween so that the cutting means 216' can sever the valve cusps 118. The strut members 232' may also be collapsible to the first condition with the severed valve cusps 118 attached to the cusp hooks 538' for retraction and removal through the blood vessel 108, optionally through the second catheter assembly 846.

The strut members 232' may have a different configuration when associated with the second catheter assembly 846 than when associated with the first catheter assembly 210. As best shown in FIG. 10, the strut members 232' associated with the second catheter assembly 846 approach the cardiac valve 106 from the opposite direction of the first catheter assembly 210. Since cardiac valves 106 have a directional orientation, the cusp hooks 538' optionally have a "fishhook"-like structure, as depicted in FIGS. 10-11, when the valve cusps 118 are grasped using the second catheter assembly 846. However, any suitable configuration of the strut members 232' may be provided, regardless of the direction from which the strut members 232' approach the cardiac valve 106.

The operation of an exemplary embodiment of the present invention is shown in the sequence of FIGS. 12-19. FIG. 12 depicts an apparatus 104 for endovascular removal of a cardiac valve 106 having at least two valve cusps 118. The apparatus 104 may be reusable or may be a one-time-use item, but in any case is shown in FIG. 12 in an undeployed (or previously deployed but repacked for reuse) state.

The apparatus 104 includes a first catheter assembly 210. The apparatus 104 as shown in the exemplary embodiment of FIGS. 12-19 includes cutting means 216, at least one strut member 232 (two shown in the Figs.), and a filter assembly 222. The filter assembly 222 includes one or more filter baskets 224 (only one shown for clarity). The cutting means 216, strut members 232, and filter basket 224 are depicted in FIG. 12 in a radially collapsed first condition. Any of these or other structures/components of the apparatus 104 may be inserted to, or removed from, the blood vessel 108 as desired, in any combination or sequence needed for suitable operation in a specific application of the apparatus 104.

An exemplary embodiment of a radially collapsed cutting means 216 is shown in greater detail in FIG. 13, taken along line 13-13 of FIG. 12. However, the cutting means 216 may have any suitable radially collapsed configuration. The mechanism of collapse of the cutting means 216 will depend upon the structure of the cutting means 216, which can be readily determined for a particular application by one of ordinary skill in the art.

FIG. 14 depicts an apparatus 104 in place within a blood vessel 108 and beginning to deploy according to the present invention. The filter basket 224, having a frustoconical shape, is in a radially expanded second condition in FIG. 14, but the cutting means 216 and strut members 232 remain in the first condition.

Figure 15:
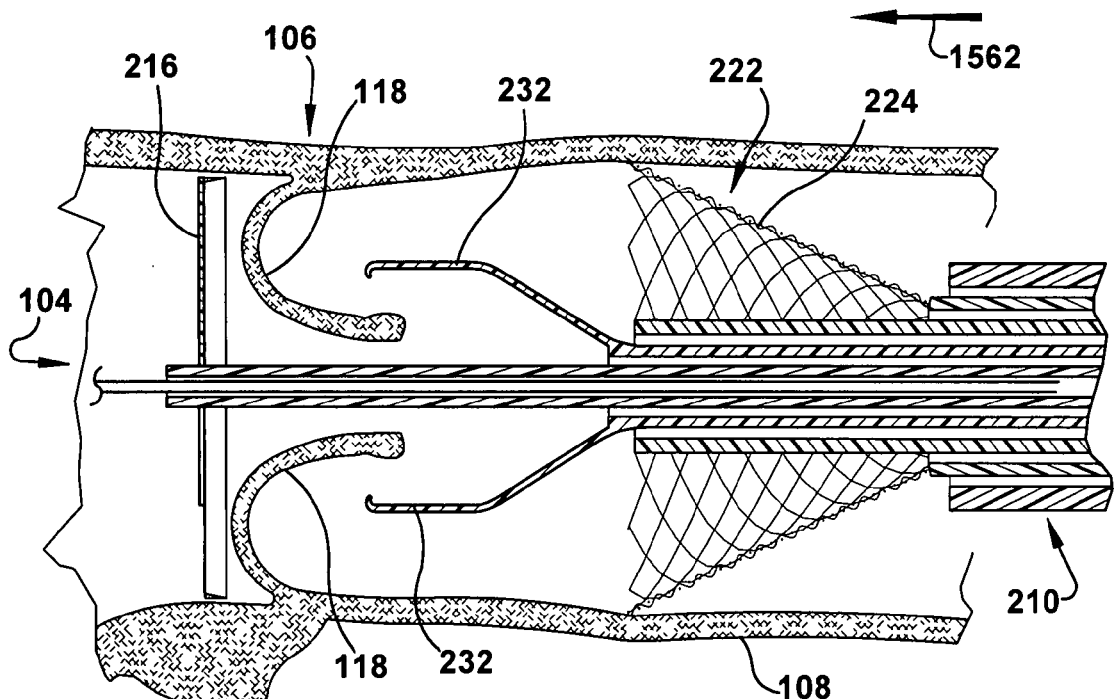
FIG. 15 is a side view similar to FIG. 14 illustrating the apparatus during a stage of the cardiac valve removal process.

In FIG. 15, the cutting means 216, filter basket 224, and strut members 232 have been expanded to the second condition adjacent the valve cusps 118. In order to expand these structures in the shown relationship adjacent to the valve cusps 118, the surgeon may advance at least a portion of the first catheter assembly 210 through the cardiac valve 106 in a first direction 1562, as shown, before deploying the cutting means 216.

Figure 16:
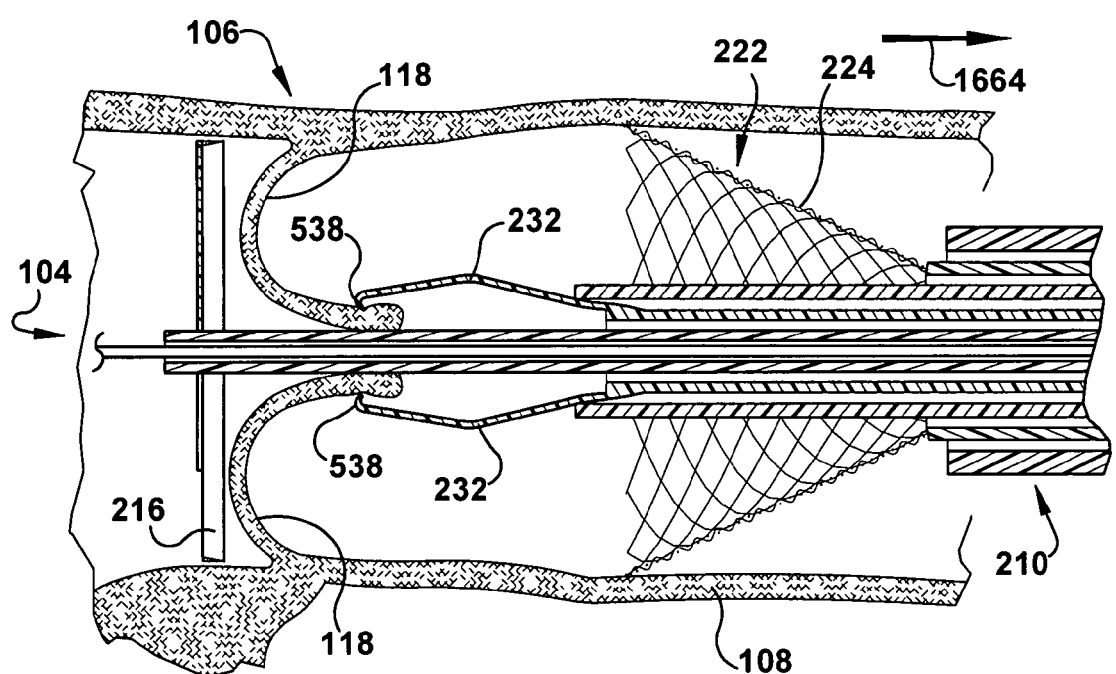
FIG. 16 is a side view similar to FIG. 14 illustrating the apparatus during another stage of the cardiac valve removal process.

FIG. 16 depicts the strut members 232 as returned to the radially collapsed first condition after having engaged the valve cusps 118 with the cusp hooks 538. This action also may substantially close the cardiac valve 106. In the exemplary embodiment of FIG. 16, a portion of the first catheter assembly 210 is interposed between the valve cusps 118 and the strut members 232 are holding the valve cusps 118 in contact with that portion of the first catheter assembly 210. The strut members 232 are optionally pulled in a second direction 1664 longitudinally opposite the first direction 1562 to close the cardiac valve 106.

Figure 17:
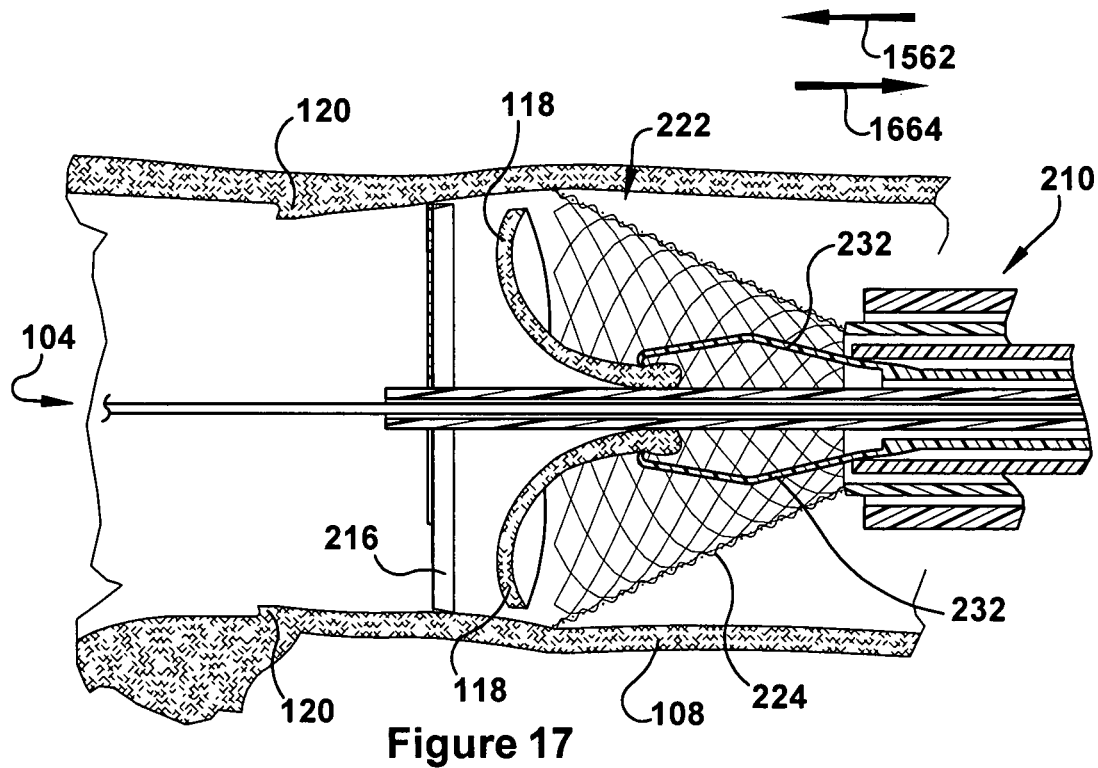
FIG. 17 is a side view similar to FIG. 14 illustrating the apparatus during another stage of the cardiac valve removal process.

FIG. 17 depicts the apparatus 104 just after having severed the valve cusps 118. The cutting means 216 has moved in the second direction 1664 (parallel to the longitudinal axis), engaging the valve cusps 118 and severing the valve cusps 118 at or near their roots 120. In FIG. 17, the strut members 232 are holding the severed valve cusps 118 against a portion of the first catheter assembly 210. If the strut members 232 release the severed valve cusps 118, whether accidentally or intentionally, at least one filter basket 224 of the filter assembly 222, when present, should capture the severed valve cusps 118 and prevent the valve cusps 118 from being carried freely through the blood vessel 108.

Figure 18:
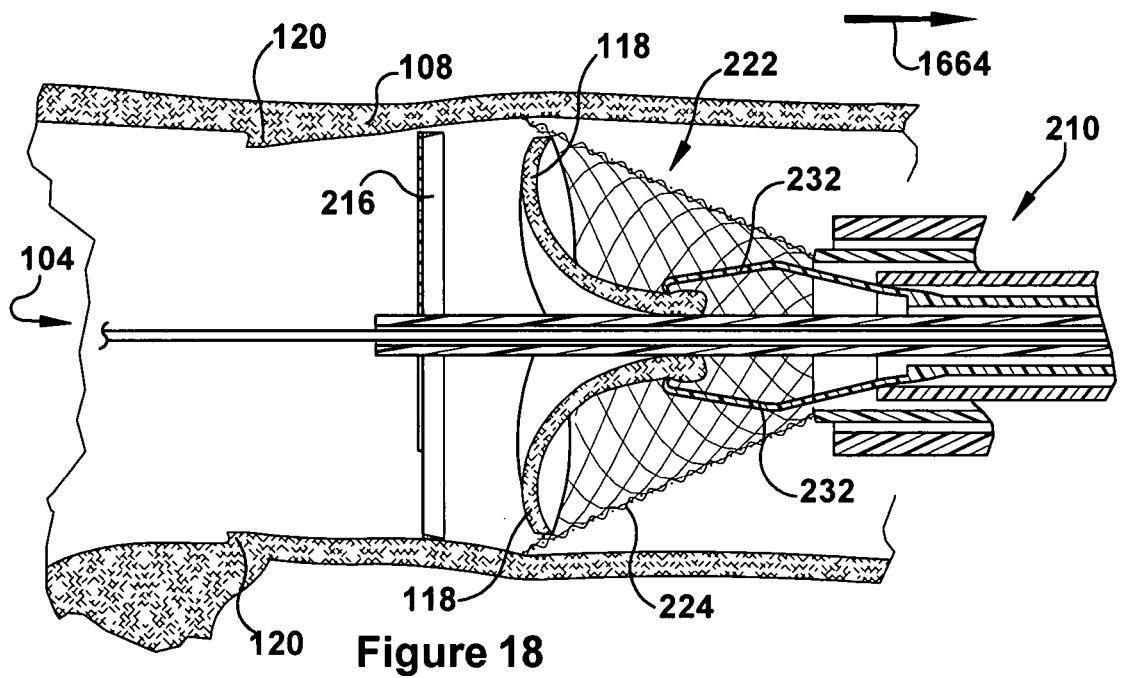
FIG. 18 is a side view similar to FIG. 14 illustrating the apparatus during another stage of the cardiac valve removal process.

In the portion of the valve removal sequence shown in FIG. 18, the strut members 232 are being pulled back into the filter assembly 222 and the severed valve cusps 118 are collected in the filter assembly 222. Optionally, collecting the severed valve cusps 118 in the filter assembly 222 includes engaging the severed valve cusps 118 with at least one of the filter baskets 224.

If valve removal debris is generated by the severing of the valve cusps 118, the valve removal debris may also be collected in a filter basket 224. To provide desired bloodflow characteristics in the blood vessel 108, multiple filter baskets 224 having differing porosities may be provided. For example, a wide-mesh filter basket 224 may capture the severed valve cusps 118 but allow most valve removal debris to pass through. The valve removal debris may then be collected in a second filter basket 224 having a finer mesh size.

In the exemplary embodiment of FIG. 18, the strut members 232 are shaped such that contact with a portion of the first catheter assembly 210 tends to urge the strut members toward the first condition as the strut members 232 are pulled back into the filter assembly 222. This shaping and contact helps the strut members 232 grasp the severed valve cusps 118 more firmly.

In combination with collecting the severed valve cusps 118 or after the severed valve cusps 118 are collected, the filter assembly 222, strut members 232, and cutting means 216 are collapsed back to their respective first conditions. For example, each structure may be pulled in the second direction 1664 and radially collapse upon engagement with a portion of the first catheter assembly 210. The collapse of each structure may be accomplished in any suitable sequence or manner and need not depend upon a mere reversal of the motions taken to deploy that structure. Certain structures, such as the cutting means 216, may even be released by the apparatus 104 and collected within the filter assembly 222 by the strut members 232 or suction device 640 in much the same manner as released severed valve cusps 118 are collected. It is also contemplated by the present invention that certain structures, such as the cutting means 216, could be completely removed from the body via movement in the second direction through the first catheter assembly 210 separately from the remaining structures of the assembly 104.

Figure 19:
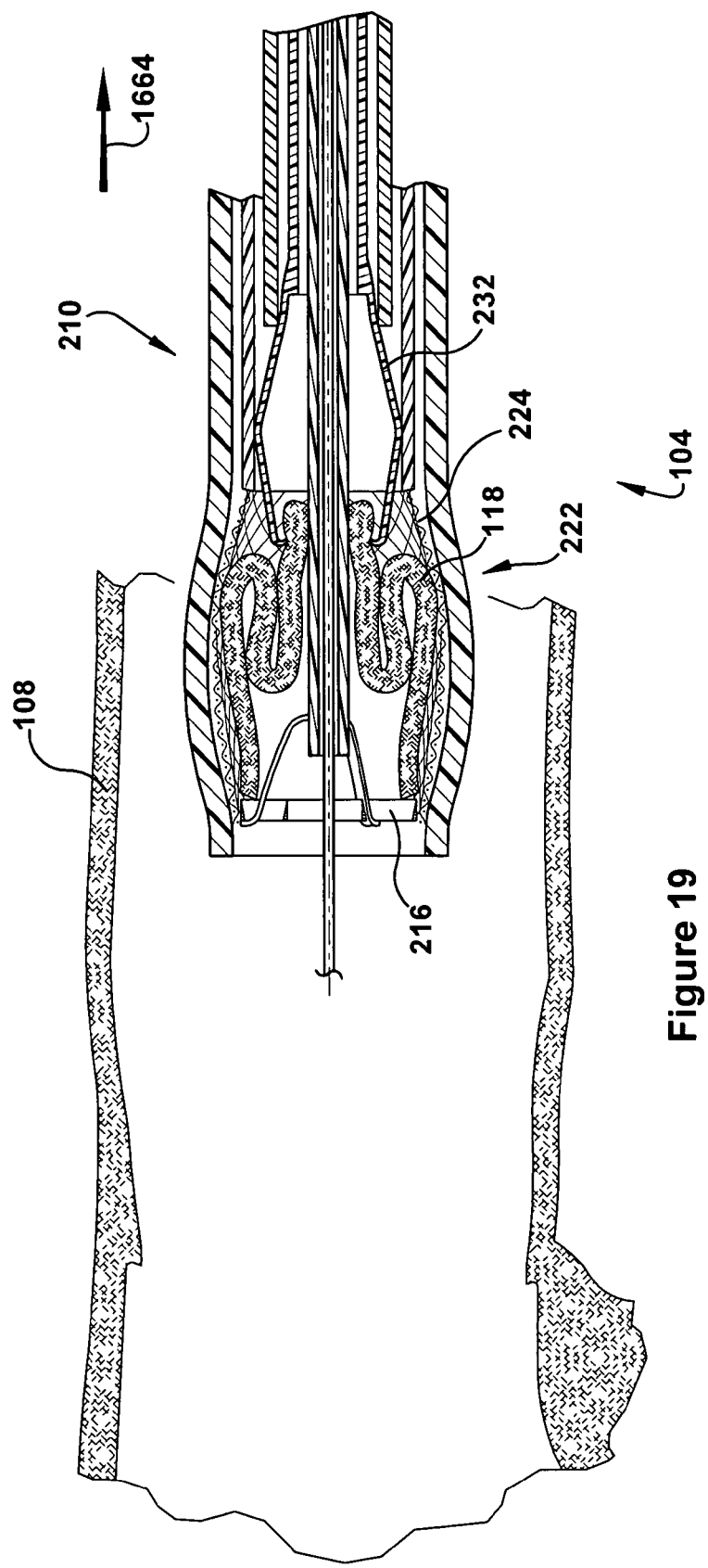
FIG. 19 is a side view similar to FIG. 14 illustrating the apparatus in the fully collapsed condition following removal of the cardiac valve.

FIG. 19 depicts an exemplary embodiment of the apparatus 104 with the filter assembly 222, strut members 232, and cutting means 216 in the first condition, and with the severed valve cusps 118 retained within the filter assembly 222. The apparatus 104 may then be withdrawn from the blood vessel 108 by pulling the first catheter assembly 210 in the second direction 1664. Removal of the cardiac valve 106 is complete at this stage.

Figure 20:
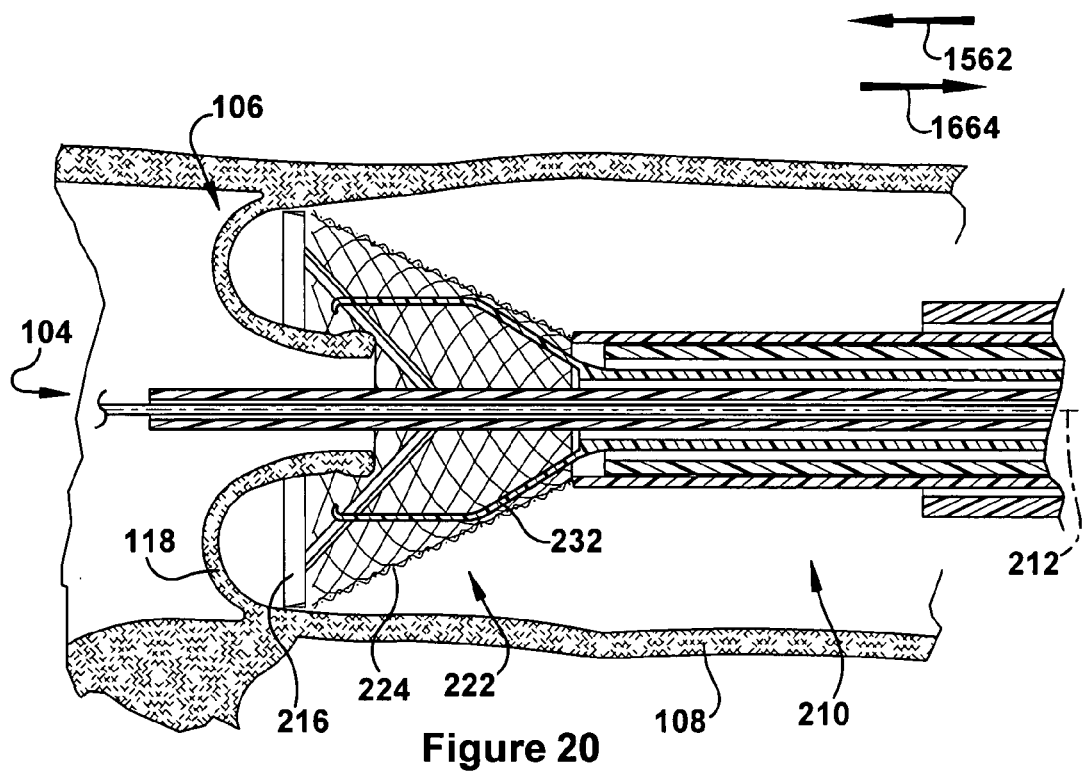
FIG. 20 is a side view, taken in section, of an apparatus for assisting in the removal of a cardiac valve in accordance with another exemplary embodiment of the present invention, illustrated in a partially deployed condition in a blood vessel adjacent a cardiac valve.
Figure 21:
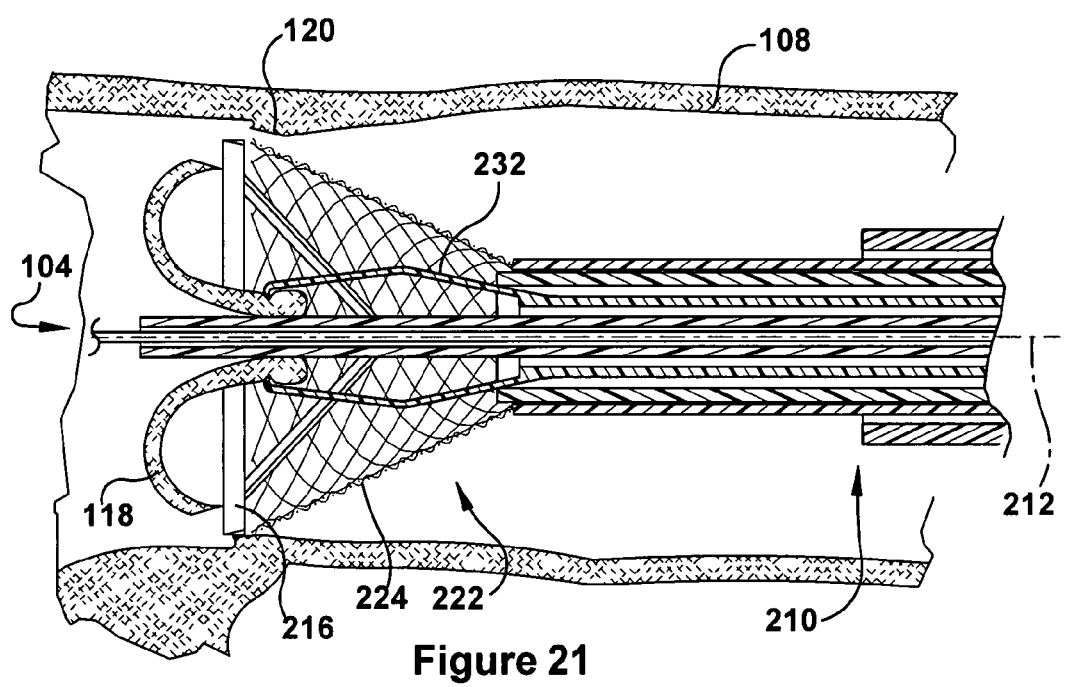
FIG. 21 is a side view similar to FIG. 20 illustrating the apparatus during a stage of the cardiac valve removal process.

FIGS. 20-21 sequentially depict the operation of an exemplary embodiment of the apparatus 104 in which the cutting means 216 travels parallel to the longitudinal axis 212 in the first direction 1562. The cutting means 216 is pushed in the first direction 1562 to sever the valve cusps 118. In this embodiment, the first catheter assembly 210 does not need to pass through the cardiac valve 106 before the valve cusps 118 are severed. However, and as shown in FIGS. 20-21, a portion of the first catheter assembly 210 may pass through the cardiac valve 106 for guidance or valve cusp 118 for support, or for any other reason.

In addition to or instead of longitudinal motion of the cutting means 216 in any embodiment of the present invention, the act of severing the valve cusps 118 may include rotating the cutting means about the longitudinal axis 212.

Figure 22:
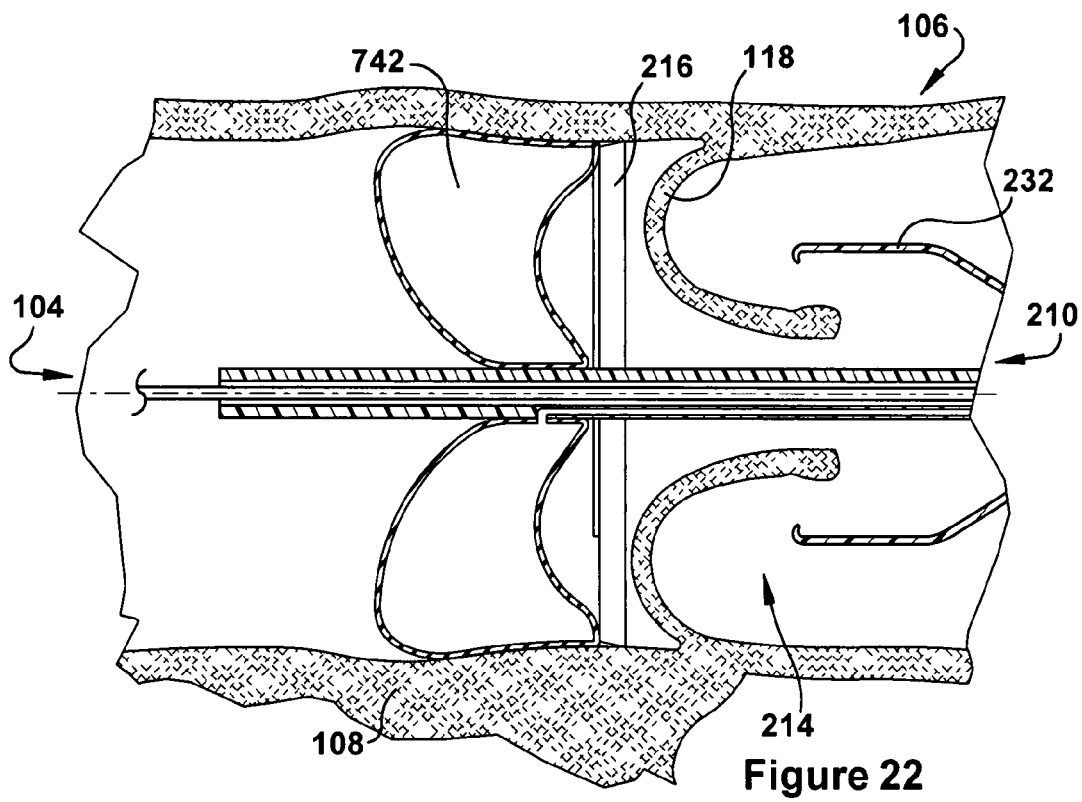
FIG. 22 is a side view, taken in section, of an apparatus for assisting in the removal of a cardiac valve in accordance with another exemplary embodiment of the present invention, illustrated in a partially deployed condition in a blood vessel adjacent a cardiac valve.
Figure 23:
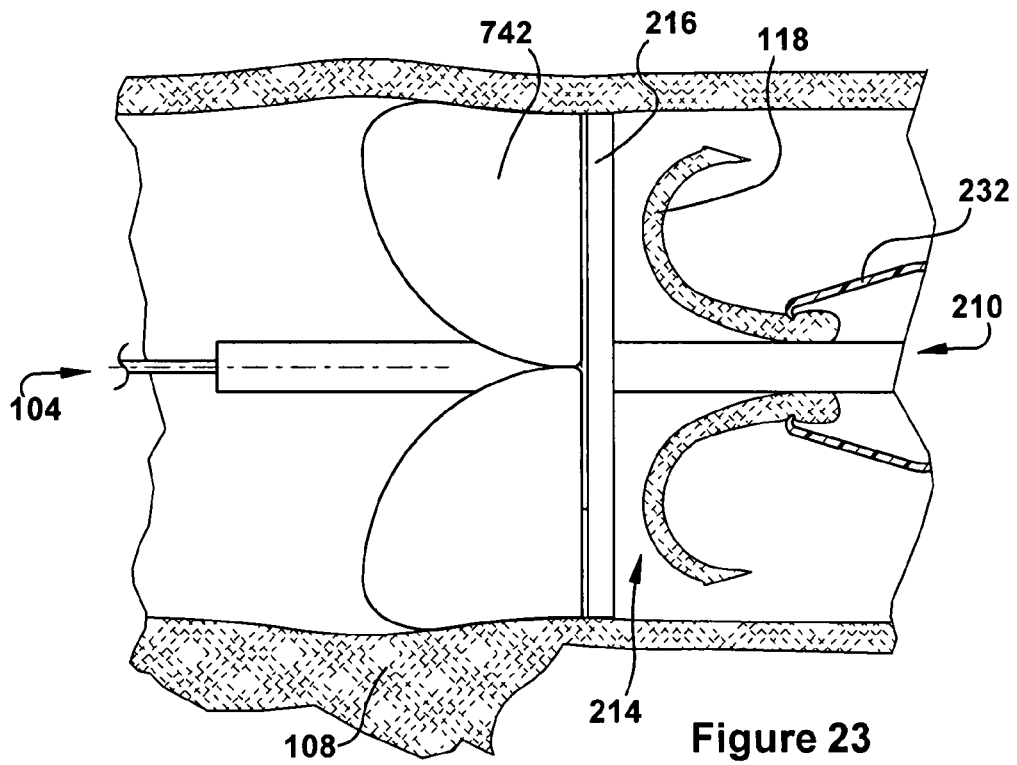
FIG. 23 is a side view similar to FIG. 22 illustrating the apparatus during a stage of the cardiac valve removal process.

FIGS. 22-23 sequentially depict the operation of an exemplary embodiment of the apparatus 104 in which at least one temporary valve flap 742 is provided to the blood vessel 108 as previously discussed. The flap 742 may be deployed at any time before, during, or after the removal sequence of the cardiac valve 106 and optionally remains in place in the blood vessel 108 after withdrawal of the apparatus 104. The flap 742 depicted in FIGS. 22-23 is a balloon flap 742 attached at the distal end 214 of the first catheter assembly 210. The balloon flap 742 may be selectively inflated and deflated to mimic the function of a native cardiac valve 106.

Figure 24:
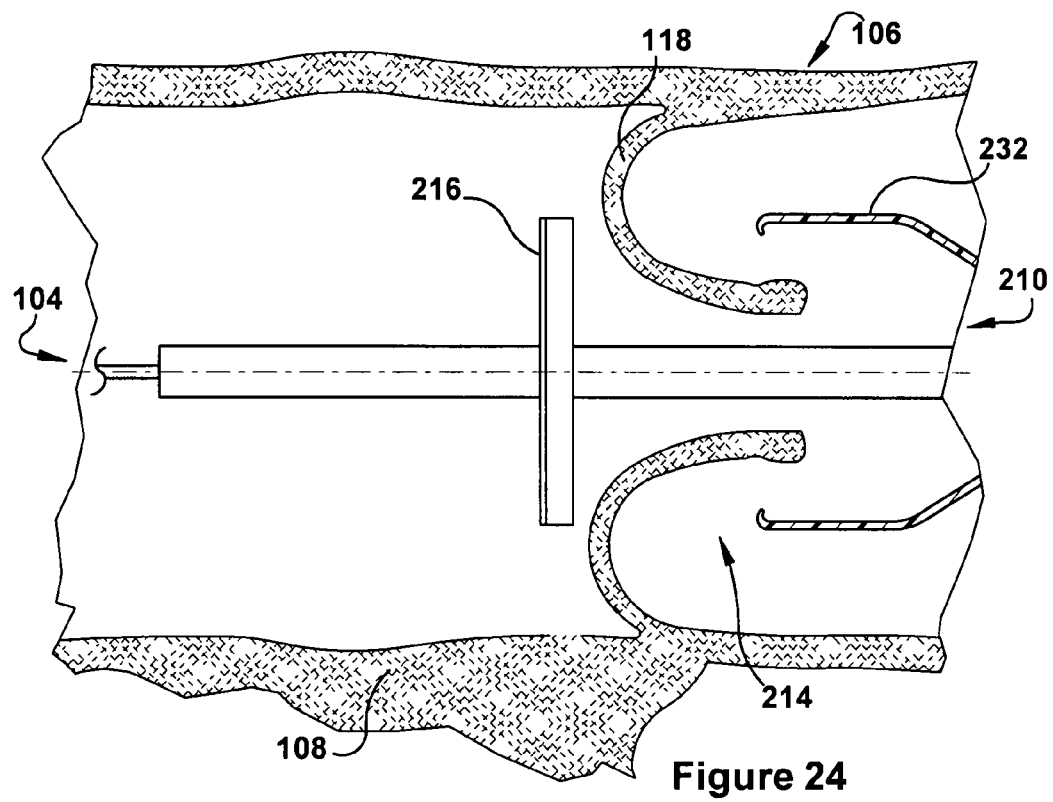
FIG. 24 is a side view, taken in section, of an apparatus for assisting in the removal of a cardiac valve in accordance with another exemplary embodiment of the present invention, illustrated in a partially deployed condition in a blood vessel adjacent a cardiac valve.
Figure 25:
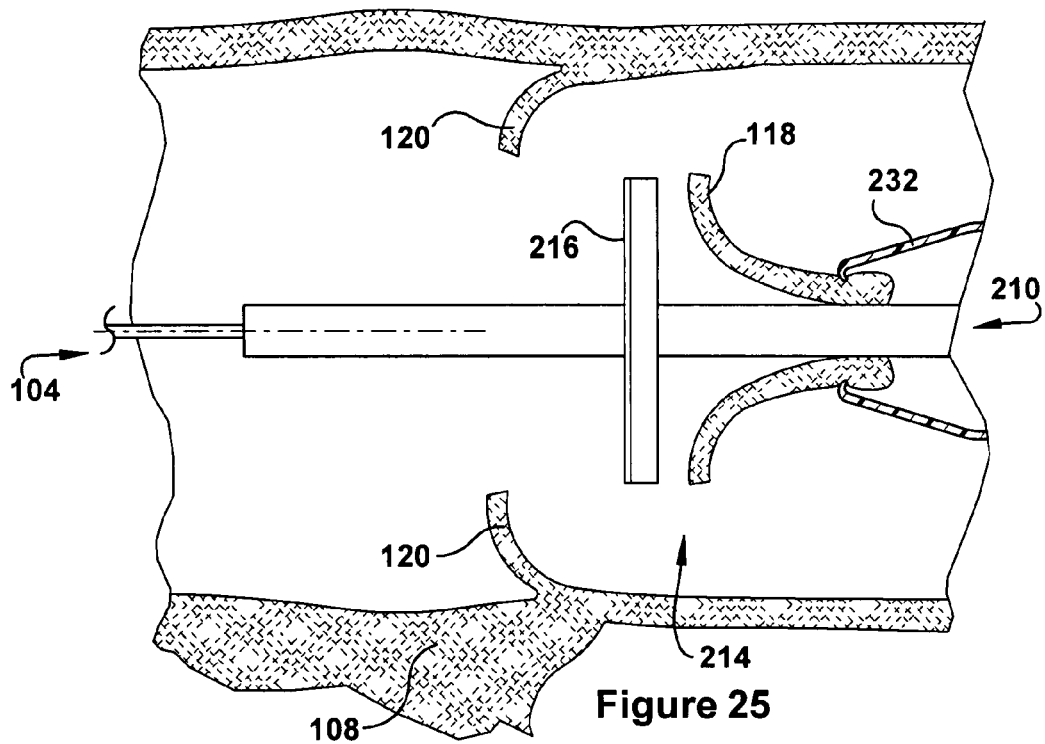
FIG. 25 is a side view similar to FIG. 24 illustrating the apparatus during a stage of the cardiac valve removal process.

FIGS. 24-25 sequentially depict the operation of an exemplary embodiment of the apparatus 104 in which the valve cusps 118 are only partially severed. This may be desirable in a situation where calcification or thrombus formation has occurred near the roots 120 of the valve cusps 118, or the surgeon wishes to sever only a portion of the valve cusps 118 for another reason. Such partial severance may avoid disturbing any present calcification or thrombus, thus reducing the possibility of creating valve removal debris during the severance of the valve cusps 118. This exemplary embodiment operates in a similar manner to those embodiments previously described. However, in the present exemplary embodiment, the cutting means 216 spans less than the entire diameter of the blood vessel 108, as shown in FIGS. 24-25. In contrast, the cutting means 216 will substantially span the blood vessel 108 diameter when the valve cusps 118 are to be completely severed from their roots 120; for example, in the exemplary embodiments of FIGS. 20-21 and 22-23.

While aspects of the present invention have been particularly shown and described with reference to the preferred embodiment above, it will be understood by those of ordinary skill in the art that various additional embodiments may be contemplated without departing from the spirit and scope of the present invention. For example, the number, positioning, and/or dimensions of filter baskets 224 may differ from those described. The strut members 232 may grasp or move in a different manner. The first and second catheter assemblies 210 and 742 may be inserted into different blood vessels 108 or in a different sequence. Valve cusps 118 could be grasped or severed singly or concurrently. Radiopaque markers or an endoscope could be included in the apparatus 104 to facilitate operation thereof. A prosthetic valve could be installed with assistance of at least a portion of the apparatus 104. However, a device or method incorporating such an embodiment should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, the following is claimed:

1. An apparatus for endovascular removal of a cardiac valve having at least two valve cusps, the apparatus being insertible through a blood vessel to access the cardiac valve, the apparatus comprising:
   a first catheter assembly for insertion into a blood vessel, the first catheter assembly having a longitudinal axis and a distal end;
   deployable cutting means for cutting at least one valve cusp of the cardiac valve, the cutting means being attached to the distal end of the first catheter assembly; and
   a deployable filter assembly disposed adjacent the distal end of the first catheter assembly and including at least two filter baskets, the filter assembly being operable to collect the severed valve cusps and being collapsible for removal from the blood vessel with the at least two severed valve cusps retained therein, at least two strut members, each of the at least two strut members having a first end connected with the first catheter assembly adjacent the distal end, each of the at least two strut members further having a second end comprising a cusp hook, the at least two strut members being operable to grasp and close the at least two valve cusps of a cardiac valve therebetween so that the cutting means can sever the valve cusps.

2. The apparatus of claim 1, wherein each of the filter baskets has a frustoconical shape.

3. The apparatus of claim 1, wherein the at least two filter baskets are disposed adjacent to each other along the longitudinal axis and, when deployed, axially overlap at least a portion of one another.

4. The apparatus of claim 1, wherein the at least two filter baskets have different porosities.

5. The apparatus of claim 1, wherein first and second filter baskets are located adjacent a first side of the cutting means and a third filter basket is located adjacent a second side of the cutting means longitudinally spaced from the first side.

6. The apparatus of claim 1, wherein at least one filter basket includes a filter rim spaced radially apart from the distal end of the first catheter assembly and the filter rim includes the cutting means.

7. The apparatus of claim 1, wherein the at least two strut members comprise a pair of strut members spaced evenly apart about the longitudinal axis of the first catheter assembly.

8. The apparatus of claim 1, wherein the at least two strut members comprise three strut members spaced evenly apart about the longitudinal axis of the first catheter assembly.

9. The apparatus of claim 1, further comprising a sheath for encircling the at least two strut members.

10. The apparatus of claim 1, further comprising means for moving the at least two strut members between a radially collapsed first condition and a radially expanded second condition.

11. The apparatus of claim 10, wherein the at least two strut members are collapsible to the first condition with the at least two severed cusps attached to the cusp hooks for retraction and removal through the blood vessel.

12. The apparatus of claim 1, including a suction device disposed adjacent the cutting means, wherein the cutting means produces valve removal debris while severing at least one valve cusp and the suction device is adapted to draw at least one of the valve removal debris and the severed valve cusp into the first catheter assembly.

13. The apparatus of claim 12, wherein the suction device is a suction ring spaced radially apart from the distal end of the first catheter assembly.

14. The apparatus of claim 13, wherein at least one filter basket includes a filter rim spaced radially apart from the distal end of the first catheter device, and the suction ring is connected with the filter rim.

15. The apparatus of claim 1, further comprising at least one flap at the distal end of the first catheter assembly, the at least one flap being operable to function as a temporary valve cusp after the cardiac valve has been severed.

16. The apparatus of claim 15, wherein the at least one flap comprises an inflatable balloon.

17. An apparatus for endovascular removal of a cardiac valve having at least two valve cusps, the apparatus being insertible through a blood vessel to access the cardiac valve, the apparatus comprising:
   a first catheter assembly for insertion into a blood vessel, the first catheter assembly having a longitudinal axis and a distal end;
   cutting means for cutting at least one valve cusp of the cardiac valve, the cutting means being attached to the distal end of the first catheter assembly and being movable between a radially collapsed first condition and a radially expanded second condition;
   at least two strut members, each of the at least two strut members having a first end connected with the first catheter assembly adjacent the distal end, each of the at least two strut members further having a second end comprising a cusp hook, the at least two strut members being movable between a collapsed condition and an expanded condition;
   the at least two strut members, in the expanded condition, being operable to grasp and close the at least two valve cusps of a cardiac valve so that the cutting means, in the second condition, can sever the valve cusps through movement of the cutting means in the blood vessel; and a filter assembly disposed adjacent the distal end of the first catheter assembly and including at least one filter basket, the filter assembly being movable between a radially collapsed undeployed condition and a radially expanded deployed condition in which the filter assembly is operable to collect the severed valve cusps, the filter assembly being collapsed to the undeployed condition for removal from the blood vessel with the at least two severed valve cusps retained therein.

18. The apparatus of claim 17, wherein the at least one filter basket has a frustoconical shape.

19. The apparatus of claim 17, wherein the filter assembly includes at least two filter baskets.

20. The apparatus of claim 19, wherein the at least two filter baskets have different porosities.

21. The apparatus of claim 17, wherein the filter assembly comprises at least two filter baskets disposed adjacent to each other along the longitudinal axis and, when deployed, overlapping at least a portion of one another.

22. The apparatus of claim 17, wherein, when the filter assembly is in the deployed condition, first and second filter baskets are located adjacent a first side of the cutting means and a third filter basket is located adjacent a second side of the cutting means longitudinally spaced from the first side.

23. The apparatus of claim 17, wherein the at least one filter basket includes a filter rim spaced radially apart from the distal end of the first catheter assembly and the filter rim includes the cutting means.

24. The apparatus of claim 17, wherein the at least two strut members comprise a pair of strut members spaced evenly apart about the longitudinal axis of the first catheter assembly.

25. The apparatus of claim 17, wherein the at least two strut members comprise three strut members spaced evenly apart about the longitudinal axis of the first catheter assembly.

26. The apparatus of claim 17, further comprising a sheath for encircling the at least two strut members.

27. The apparatus of claim 17, further comprising means for moving the at least two strut members between a radially collapsed first condition and a radially expanded second condition.

28. The apparatus of claim 17, wherein the at least two strut members are collapsible to the first condition with the at least two severed cusps attached to the cusp hooks for retraction and removal through the blood vessel.

29. The apparatus of claim 17, including a suction device disposed adjacent the cutting means, wherein the cutting means produces valve removal debris while severing at least one valve cusp and the suction device is adapted to draw at least one of the valve removal debris and the severed valve cusp into the first catheter assembly.

30. The apparatus of claim 29, wherein the suction device is a suction ring spaced radially apart from the distal end of the first catheter assembly.

31. The apparatus of claim 29, wherein at least one filter basket includes a filter rim spaced radially apart from the distal end of the first catheter assembly, and the suction ring is connected with the filter rim.

32. The apparatus of claim 17 further comprising at least one flap at the distal end of the first catheter assembly, the at least one flap being operable to function as a temporary valve cusp after the cardiac valve has been severed.

33. The apparatus of claim 32 wherein the at least one flap comprises an inflatable balloon.

34. An apparatus for endovascular removal of a cardiac valve having at least two valve cusps, the apparatus being insertible through a blood vessel to access the cardiac valve, the apparatus comprising:

a first catheter assembly for insertion into a blood vessel, the first catheter assembly having a longitudinal axis and a distal end;

a second catheter assembly for insertion into a blood vessel, the second catheter assembly having a longitudinal axis and a proximal end, the proximal end of the second catheter assembly being connectable with the distal end of the first catheter assembly adjacent the cardiac valve;

cutting means for cutting at least one valve cusp of the cardiac valve, the cutting means being movable between a radially collapsed first condition and a radially expanded second condition, the cutting means being attached to at least one of the distal end of the first catheter assembly and the proximal end of the second catheter assembly;

at least two strut members, each of the at least two strut members having a first end connected with at least one of the first catheter assembly, adjacent the distal end, and the second catheter assembly, adjacent the proximal end, each of the at least two strut members further having a second end comprising a cusp hook, the at least two strut members being movable between a collapsed condition and an expanded condition;

the at least two strut members, in the expanded condition, being operable to grasp and close the at least two valve cusps of a cardiac valve so that the cutting means, in the second condition, can sever the valve cusps through movement of the cutting means in the blood vessel; and a filter assembly disposed adjacent at least one of the distal end of the first catheter assembly and the proximal end of the second catheter assembly and including at least one filter basket, the filter assembly being movable between a radially collapsed undeployed condition and a radially expanded deployed condition in which the filter assembly is operable to collect the severed valve cusps, the filter assembly being collapsed to the undeployed condition for removal from the blood vessel with the at least two severed valve cusps retained therein.

35. The apparatus of claim 34, wherein the at least one filter basket has a frustoconical shape.

36. The apparatus of claim 34, wherein the filter assembly includes at least two filter baskets.

37. The apparatus of claim 36, wherein the at least two filter baskets have different porosities.

38. The apparatus of claim 34, wherein the filter assembly comprises at least two filter baskets disposed adjacent to each other along the longitudinal axis and, when deployed, overlapping at least a portion of one another.

39. The apparatus of claim 34, wherein, when the filter assembly is in the deployed condition, first and second filter baskets are located adjacent a first side of the cutting means and a third filter basket is located adjacent a second side of the cutting means longitudinally spaced from the first side.

40. The apparatus of claim 34, wherein the at least one filter basket includes a filter rim spaced radially apart from the distal end of the first catheter assembly and the filter rim includes the cutting means.

41. The apparatus of claim 34, wherein the at least two strut members comprise a pair of strut members spaced evenly apart about at least one of the longitudinal axis of the first catheter assembly and the longitudinal axis of the second catheter assembly.

42. The apparatus of claim 34, wherein the at least two strut members comprise three strut members spaced evenly apart about at least one of the longitudinal axis of the first catheter assembly and the longitudinal axis of the second catheter assembly.

43. The apparatus of claim 34, further comprising a sheath for encircling the at least two strut members.

44. The apparatus of claim 34, further comprising means for moving the at least two strut members between a radially collapsed first condition and a radially expanded second condition.

45. The apparatus of claim 34, wherein the at least two strut members are collapsible to the first condition with the at least two severed cusps attached to the cusp hooks for retraction and removal through the blood vessel.

46. The apparatus of claim 34, including a suction device disposed adjacent at least one of the distal end of the first catheter assembly and the proximal end of the second catheter assembly, wherein the cutting means produces valve removal debris while severing at least one valve cusp and the suction device is adapted to draw at least one of the valve removal debris and the severed valve cusp into at least one of the first and second catheter assemblies.

47. The apparatus of claim 46, wherein the suction device is a suction ring spaced radially apart from at least one of the distal end of the first catheter assembly and the proximal end of the second catheter assembly.

48. The apparatus of claim 47, wherein at least one filter basket includes a filter rim spaced radially from at least one of the distal end of the first catheter assembly and the proximal end of the second catheter assembly, and the suction ring is connected with the filter rim.

49. The apparatus of claim 34 further comprising at least one flap adjacent at least one of the distal end of the first catheter assembly and the proximal end of the second catheter assembly, the at least one flap being operable to function as a temporary valve cusp after the cardiac valve has been severed.

50. The apparatus of claim 49 wherein the at least one flap comprises an inflatable balloon.

51. A method for endovascular removal of a cardiac valve having at least two valve cusps, the method comprising the steps of:
providing a first catheter assembly having cutting means, at least two strut members, and a filter assembly having at least two filter baskets, the cutting means being connected with a distal end of the first catheter assembly, the at least two strut members being connected with the first catheter assembly adjacent the distal end, the filter assembly being disposed near the distal end of the first catheter assembly;
inserting the distal end of the first catheter assembly through a blood vessel with the cutting means, the at least two strut members, and the filter assembly in respective radially collapsed conditions;
advancing the distal end of the first catheter assembly toward the cusps of a cardiac valve so that the cutting means, the at least two strut members, and the filter assembly are located adjacent the cusps;
expanding the cutting means, the at least two strut members, and the filter assembly to respective radially expanded conditions;
hooking the cusps of the cardiac valve with the cusp hooks on the at least two strut members;
engaging the roots of the cusps of the cardiac valve with the cutting means;
severing the cusps at or near their roots through movement of the cutting means;
pulling the at least two strut members into the filter assembly and collecting the severed cusps in the filter assembly;
collapsing the cutting means, the at least two strut members, and the filter assembly to their respective radially collapsed conditions; and
withdrawing the distal end of the first catheter assembly from the blood vessel with the severed valve cusps retained within the filter assembly.

52. The method of claim 51, wherein the step of expanding the cutting means, the at least two strut members, and the filter assembly to respective radially expanded conditions includes the step of expanding at least two filter baskets, adjacent each other along the first catheter assembly, to respective frusto-conical shapes.

53. The method of claim 51, further comprising the step of closing the cardiac valve by pulling on the at least two strut members following the step of hooking the cusps of the cardiac valve with the cusp hooks.

54. The method of claim 51, wherein the step of severing the cusps includes moving the cutting means in the axial direction.

55. The method of claim 51, wherein the step of severing the cusps includes rotating the cutting means about the longitudinal axis.

56. The method of claim 51, wherein the step of severing the cusps at or near their roots through movement of the cutting means includes the step of producing valve removal debris.

57. The method of claim 56, wherein the step of pulling the at least two strut members into the filter assembly and collecting the severed cusps in the filter assembly includes providing a suction device disposed adjacent the cutting means and applying suction to draw at least one of the valve removal debris and the severed cusps into the filter assembly.

58. The method of claim 51, wherein the step of pulling the at least two strut members into the filter assembly and collecting the severed cusps in the filter assembly includes engaging at least one of the valve removal debris and the severed cusps with at least one of the filter baskets.

59. The method of claim 51, wherein the at least two filter baskets have differing porosities.

60. The method of claim 51, further comprising the step of deploying a temporary valve which mimics the function of the cardiac valve in the blood vessel.

61. The method of claim 60, wherein the step of deploying a temporary valve comprises inflating at least one balloon flap attached at the distal end of the first catheter assembly.

62. A method for endovascular removal of a cardiac valve having at least two valve cusps, the method comprising the steps of:
providing a first catheter assembly having a distal end with cutting means connected at the distal end, the cutting means being movable between a radially collapsed first condition and a radially expanded second condition, the first catheter assembly further including at least two strut members and a filter assembly, the at least two strut members being attached to the first catheter assembly adjacent the distal end, each of the at least two strut members having an end comprising a cusp hook, the at least two strut members being movable between a collapsed condition and an expanded condition, the filter assembly having at least two filter baskets and being disposed near the distal end of the first catheter assembly, the filter assembly being movable between a radially collapsed undeployed condition and a radially expanded deployed condition;

placing the cutting means in the first condition;
placing the at least two strut members in the collapsed condition;
placing the filter assembly in the undeployed condition;
inserting the distal end of the first catheter assembly through a blood vessel;
advancing the distal end of the first catheter assembly toward the cusps of a cardiac valve so that the cutting means, the at least two strut members, and the filter assembly are located adjacent the cusps;
deploying the filter assembly to the deployed condition;
expanding the at least two filter baskets of the filter assembly, adjacent each other along the first catheter assembly, to respective frustoconical shapes;
expanding the cutting means to the second condition;
moving the at least two strut members to the expanded condition and into engagement with the cusps of the cardiac valve;
hooking the cusps of the cardiac valve with the cusp hooks on the at least two strut members;
closing the cardiac valve by moving the at least two strut members;
engaging the cusps of the cardiac valve with the cutting means;
severing the cusps at or near their roots through movement of the cutting means;
pulling the at least two strut members into the filter assembly and collecting the severed cusps, which are attached to the at least two strut members, in the filter assembly;
collapsing the at least two strut members to the collapsed condition;
collapsing the filter assembly to the undeployed condition with the valve cusps contained therein;
collapsing the cutting means to the first condition; and
withdrawing the distal end of the first catheter assembly from the blood vessel with the severed valve cusps retained within the filter assembly in the undeployed condition.

63. The method of claim 62, including the steps of:
providing a second catheter assembly having a longitudinal axis and a proximal end;
inserting the proximal end of the second catheter assembly through a blood vessel; and
engaging the distal end of the first catheter assembly with the proximal end of the second catheter assembly within the blood vessel.

* * * * *